US006331617B1

(12) United States Patent
Weeks et al.

(10) Patent No.: US 6,331,617 B1
(45) Date of Patent: **\*Dec. 18, 2001**

(54) POSITIVELY CHARGED OLIGONUCLEOTIDES AS REGULATORS OF GENE EXPRESSION

(75) Inventors: Daniel L. Weeks; John Dagle, both of Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/049,277

(22) Filed: Mar. 27, 1998

Related U.S. Application Data

(63) Continuation-in-part of application No. 08/619,301, filed on Mar. 21, 1996, now Pat. No. 5,734,040.

(51) Int. Cl.[7] ............................ C07H 21/04; C07H 19/00; A01N 43/04

(52) U.S. Cl. ....................... 536/24.5; 536/22.1; 536/23.1; 536/24.3; 514/44

(58) Field of Search .................. 536/24.5, 22.1, 536/23.1, 24.3; 514/44

(56) References Cited

U.S. PATENT DOCUMENTS

| | | | |
|---|---|---|---|
| 5,175,266 | 12/1992 | Varma et al. | 536/22 |
| 5,176,996 | 1/1993 | Hogan et al. | 435/6 |
| 5,194,654 | 3/1993 | Hostetler et al. | 558/152 |
| 5,407,801 | 4/1995 | Miller | 435/6 |
| 5,476,925 | 12/1995 | Letsinger et al. | 536/23.1 |
| 5,489,677 | 2/1996 | Sanghvi et al. | 536/22.1 |
| 5,563,253 | 10/1996 | Agrawal et al. | 536/22.1 |
| 5,646,261 | 7/1997 | Uhlmann et al. | 536/24.3 |
| 5,734,040 | 3/1998 | Weeks et al. | 536/24.5 |

FOREIGN PATENT DOCUMENTS

| | | |
|---|---|---|
| 0 522 767 A2 | 7/1993 | (EP) . |
| WO 90/14074 | 11/1990 | (WO) . |
| WO 92/10590 | 6/1992 | (WO) . |
| WO 93/07295 | 4/1993 | (WO) . |
| WO 93/10820 | 6/1993 | (WO) . |
| WO 93/12135 | 6/1993 | (WO) . |
| WO 93/24507 | 12/1993 | (WO) . |
| WO 94/06811 | 3/1994 | (WO) . |
| WO 94/11524 | 5/1994 | (WO) . |
| WO 94/15616 | 7/1994 | (WO) . |
| WO 94/17091 | 8/1994 | (WO) . |
| WO 94/24144 | 10/1994 | (WO) . |
| WO 95/17373 | 6/1995 | (WO) . |
| WO 95/20404 | 8/1995 | (WO) . |

OTHER PUBLICATIONS

A.H. Aleem et al., "Synthesis of Carboxamide Linked Dimers, T\* T and 4 $U^{Cl}$\* T.—Duplex and Triplex Stabilities of the Corresponding Oligodeoxynucleotides," *Tetrahedron*, 51 7867–7876 (1995).

C.P. Bailey et al., "Cationic Oligonucleotides as Specific Inhibitors of Gene Expression," Abstract from Weinstein Meeting on Heart Development, May 28–31, Vanderbilt University, Nashville, TN (1998).

A. Castro et al., "Single–Molecule Detection of Specific Nucleic Acid Sequences in Unamplified Genomic DNA," *Anal. Chem.*, 69 3915–3920 (1997).

S. Chaturvedi et al., "Stabilization of triple–stranded oligonucleotide complexes: use of probes containing alternating phosphodiester and stereo–uniform cationic phosphoramidate linkages", *Nucleic Acids Research*, 24 2318–2323 (1996).

(List continued on next page.)

*Primary Examiner*—Jezia Riley
(74) *Attorney, Agent, or Firm*—Mueting, Raasch & Gebhardt, P.A.

(57) ABSTRACT

This invention relates to oligonucleotides with cationic phosphoramidate internucleoside linkages useful for binding to nucleic acid to inhibit or alter gene expression.

31 Claims, 4 Drawing Sheets

Methoxyethylamine
Phosphoramidate
(\*)

N,N-Diethylethylenediamine
Phosphoramidate
(+)

OTHER PUBLICATIONS

A.J. Cheng et al., "Monovalent Cation Effects on Intermolecular Purine–Purine–Pyrimidine Triple–Helix Formation," *Nucleic Acids Res.*, 21 5630–5635 (1993).

J.M. Dagle, "Positively Charged Oligonucleotides Overcome Potassium–Mediated Inhibition of Triplex DNA Formation", *Nucleic Acids Research*, 24 2143–2149 (1996).

J.M. Dagel et al., "Physical Properties of Oligonucleotides Containing Phosphoramidate–Modified Internucleoside Linkages," *Nucleic Acids Research*, 19 1805–1810 (1991).

R. Fathi et al., "Oligonucleotides with novel, cationic backbone substituents: aminoethylphosphonates", *Nucleic Acids Research*, 22 5416–5424 (1994).

S. P. A. Fodor, "DNA Sequencing: Massively Parallel Genomics," *Science*, 277 393–395 (1997).

E.R. Kandimalla et al., "Single–Strand–Targeted Triplex Formation: Stability, Specificity and RNase H Activation Properties," *Gene*, 149 115–121 (1994).

I.V. Kutyavin et al., "Efficient, Specific Interstrand Cross–Linking of Double–Stranded DNA by a Chlorambucil–Modified, Triplex–Forming Oligonucleotide," *J. Am. Chem. Soc.*, 115 9303–9304 (1993).

E.S. Lander, "The New Genomics: Global Views of Biology," *Science*, 274 536–539 (1996).

L.J. Maher III et al., "Inhibition of DNA/Protein Interactions by Oligonucleotide–Directed DNA Triple Helix Formation: Progress and Prospects", *Prospects for Antisense Nucleic Acid Therapy of Cancer and AIDS*, 227–242 (1991).

J.F. Milligan et al., "An Anti–Parallel Triple Helix Motif with Oligodeoxynucleotides Containing 2'–deoxyguanosine and 7–deaza–2'–deoxyxanthosine," *Nucleic Acids Res.*, 21 327–333 (1993).

W.M. Olivas et al., "Overcoming potassium–mediated triplex inhibition", *Nucleic Acids Research*, 23 1936–1941 (1995).

H. Ørum et al., "Sequence–Specific Purification of Nucleic Acids by PNA–Controlled Hybrid Selection," *BioTechniques*, 19 472–480 (1995).

J.D. Potts et al., "Epithelial–Mesenchymal Transformation of Embryonic Cardiac Endothelial Cells is Inhibited by a Modified Antisense Oligodioxynucleotide to Transforming Growth Factor β3," *PNAS (USA)*, 88 1516–1520 (1991).

P.L. Ross et al., "Discrimination of Single–Nucleotide Polymorphisms in Human DNA Using Peptide Nucleic Acid Probes Detected by MALDI–TOF Mass Spectometry," *Anal. Chem.*, 69 4197–4202 (1997).

J.G. Schmidt et al., "Information Transfer from Peptide Nucleic Acids to RNA by Template–Directed Syntheses," *Nucleic Acids Res.*, 25 4797–4802 (1997).

T.J. Stonehouse et al., "DNase I footprinting of triple helix formation at polyprine tracts by acridine–linked oligopyrimidines: stringency, structural changes and interaction with minor groove binding ligands", *BBA*, 1218 322–330 (1994).

R.A. Stull et al., "Antigene, Ribozyme and Aptamer Nucleic Acid Drugs: Progress and Prospects," *Pharmaceutical Res.*, 12 465–483 (1995).

C.H. Tung et al., "Polyamine–linked oligonucleotides for DNA triple helix formation", *Nucleic Acids Research*, 21 5489–5494 (1993).

P.D. Vize et al., Chapter 20 in *Methods in Cell Biology* vol. 36 entitled "Xenopus Laevis: Practical Uses in Cell and Molecular Biology," B. Kay and H. B. Peng, Eds., Academic Press, Inc., pp. 367–387 (1991).

R.Y. Walder et al., "Role of RNase H in Hybrid–Arrested Translation by Antisense Oligonucleotides," *Proc. Natl. Acad. Sci. USA*, 85 5011–5015 (1988).

D.L. Weeks et al., "Cyclin B mRNA depletion only transiently inhibits the *Xenopus* embyonic cell cycle", *Development*, 111 1173–1178 (1991).

W.D. Wilson et al., "DNA Triple–Helix Specific Intercalators As Antigene Enhancers: Unfused Aromatic Cations", *Biochem.*, 32 10614–10621 (1993).

A. Colman, "Translation of Eukaryotic Messenger RNA in Xenopus Oocytes," Chapter 10 in D. Hames and S. Higgins, (Ed.), *Transcription and Translation—A Practical Approach*, IRL Press, Oxford, pp. 271–302, (1984).

P. D. Nieuwkoop et al., Ed., *Normal Table of Xenopus Leavis (Daudin)*. North–Holland Publishing Co., Amsterdam; cover, title page, publication page, and table of contents only, 4 pages (1967).

T.S. Rao et al., "Incorporation of 2'–Deoxy–6–thioguanosine into G–Rich Oligodeoxyribonucleotides Inhibits G–Tetrad Formation and Facilitates Triplex Formation", *Biochem.*, 34 765–772 (1995).

Abstract for NIH—James A. Shannon Award "Cationic Oligonucleotides for In Vivo Triplex Formation," Oct. 1997–Oct. 1999.

Abstracts for NIH–SCOR (P50–HLA42266); Project 1: Molecular Genetic Epidemiology of Atrioventricular Canal of Perimembranous Interventricular Septal Defects; Project 2: Extracellular Matrix Interactions in Cardiac Morphogenesis; Project 3: Regulation of Endothelial/Mesenchymal Transformation in Cardiac Development: The Stepwise Control of Endothelial Cell Transformation in Endocardial Cushion; Project 4: Cytoskeleton and the Development of Endocardial–Cushions; Project 5: Role of FGF's and an Int–2 Related Protein in Cushion Tissue Morphogenesis; Jan. 1, 1995–Dec. 31, 1998.

T.M. Woolf et al., "The Stability, Toxicity and Effectiveness of Unmodified and Phosphorothioate Antisense Oligodeoxynucleotides in Xenopus Oocytes and Embryos," *Nucleic Acids Research*, 18 :7 1763–1769 (1990).

F.K. Askari et al., "Molecular Medicine Antisense–Oligonucleotide Therapy", *New Engl. J. Med.*, 334 316–318 (1996).

P.A. Beal et al., "Second Structural Motif for Recognition of DNA by Oligonucleotide–Directed Triple–Helix Formation", *Science*, 251 1360–1363 (1991).

B.L. Brizzard et al., "Immunoaffinity Purification of FLAG Epitope–Tagged Bacterial Alkaline Phosphatase Using a Novel Monoclonal Antibody and Peptide Elution", *BioTechniques*, 16 730–735 (1994).

D.A. Brown et al., "Effect of Phosphorothioate Modification of Oligodeoxynucleotides on Specific Protein Binding", *J. of Biological Chemistry*, 269 26801–26805 (1994).

S.A. Cassidy et al., "Effect of a Triplex–Binding Ligand on Parallel and Antiparallel DNA Triple Helices Using Short Unmodified and Acridine–Linked Oligonucleotides", *Biochem.*, 33 15338–15347 (1994).

M. Cooney et al., "Site–Specific Oligonucleotide Binding Represses Transcription of the Human c–*myc* Gene in Vitro", *Science*, 241 456–459 (1988).

J.M. Dagle et al., "Targeted degradation of mRNA in Xenopus oocytes and embryos directed by modified oligonucleotides: studies of An2 and cyclin in embryogenesis", *Nucleic Acids Research*, 18 4751–4757 (1990).

J.M. Dagle et al., "Pathways of Degradation and Mechanism of Action of Antisense Oligonucleotides in *Xenopus Iaevis* Embryos", *AntiSense Research and Development*, 1 11–20 (1991).

R.H. Durland et al., "Binding of Triple Helix Forming Oligonucleotides to Sites in Gene Promoters", *Biochem.*, 30 9246–9255 (1955).

R.H. Durland et al., "Binding of T and T analogs to CG base pairs in antiparallel triplexes", *Nucleic Acids Research*, 22 3233–3240 (1994).

B.C. Froehler et al., "Synthesis of DNA via deoxynucleoside H–phosphonate intermediates", *Nucleic Acids Research*, 14 5399–5407 (1986).

J.E. Fulton et al., "Functional analysis of avian class I (BFIV) glycoproteins by epitope tagging and mutagenesis in vitro", *Eur. J. Immunol.*, 25 2069–2076 (1995).

J.E. Gee et al., "Structure and Applications of Intermolecular DNA Triplexes", *Med. Sciences*, 304 366–372 (1992).

C. Giovannangeli et al., "Oligonucleotide clamps arrest DNA synthesis on a single–stranded DNA target", *Proc. Natl. Acad. Sci. USA*, 90 10013–10017 (1993).

M.A. Guvakova et al., "Phosphorothioate Oligodeoxynucleotides Bind to Basic Fibroblast Growth Factor, Inhibit Its Binding to Cell Surface Receptors, and Remove It from Low Affinity Binding Sites on Extracellular Matrix", *J. of Bio. Chem.*, 270 2620–2627 (1995).

T. Horn et al., "Oligonucleotides with Alternating Anionic and Cationic Phosphoramidate Linkages: Synthesis and Hybridization of Stereo–uniform Isomers", *Tetrahedron Letters*, 37 743–746 (1996).

S.D. Jayasena et al., "Intramolecular Triple–Helix Formation at $(Pu_nPy_n) \cdot (Pu_nPy_n)$ Tracts: Recognition of Alternate Strands via Pu •PuPy and Py •PuPy Base Triplets", *Biochem.*, 31 320–327 (1992).

S.D. Jayasena et al., "Oligonucleotide–directed triple helix formation at adjacent oligopurine and oligopyrimidine DNA tracts by alternate strand recognition", *Nucleic Acids Research*, 20 5279–5288 (1992).

D.H. Jones et al, "A Rapid Method for Recombination and Site–Specific Mutagenesis by Placing Homologous Ends on DNA Using Polymerase Chain Reaction", *BioTechniques*, 10 62–66 (1991).

H.G. Kim et al., "Inhibition of in Vitro Transcription by a Triplex–Forming Oligonucleotide Targeted to Human c–*myc* P2 Promoter", *Biochem.* 34 8165–8171 (1995).

J. Klysik, "Cruciform Extrusion Facilitates Intramolecular Triplex Formation between Distal Oligopurine •Oligopyrimidine Tracts: Long Range Effects", *J. of Bio. Chem.*, 267 17430–17437 (1992).

S.H. Krawczyk et al., "Oligonucleotide–mediated triple helix formation using an $N^3$–protonated deoxycytidine analog exhibiting pH–independent binding within the physiological range", *Proc. Natl. Acad. Sci. USA*, 89 3761–3764 (1992).

T. LeDoan et al., "Sequence–specific recognition, photocrosslinking and cleavage of the DNA double helix by an oligo[α]–thuymidylate convalently linked to an azidoproflavine derivative", *Nucleic Acids Research*, 15 7749–7760 (1987).

R.L. Letsinger et al., "Cationic Oligonucleotides", *J. of Amer. Chem. Soc.*, 110 4470–4471 (1988).

V.I. Lyamichev et al., "A stable complex between homopyrimidine oligomers and the homologous regions of duplex DNAs", *Nucleic Acids Research*, 16 2165–2178 (1988).

V.M. Macaulay et al., "Inhibition of aromatase expression by a psoralen–linked triplex–forming oligonucleotide targeted to a coding sequence", *FEBS Letters*, 372 222–228 (1995).

H.E. Moser et al., "Sequence–Specific Cleavage of Double Helical DNA by Triple Helix Formation", *Science*, 238 645–650 (1987).

M. Musso et al., "Polyamine effects on purine–purine–pyrimidine triple helix formation by phosphodiester and phosphorothioate oligodeoxyribonucleotides", *Nucleic Acids Research*, 23 2320–2327 (1995).

W.M. Olivas et al., "Competitive Triplex–Quadruplex Equilibria Involving Guanine–Rich Oligonucleotides", *Biochem.*, 34 278–284 (1995).

Z. Oláh et al., "A Cloning and ∈–Epitope–Tagging Insert for the Expression of Polymerase Chain Reaction–Generated cDNA Fragments in *Escherichia coli* and Mammalian Cells", *Anal. Biochem.*, 221 94–102 (1994).

F.M. Orson et al., "Linkage structures strongly influence the binding cooperativity of DNA intercalators conjugated to triplex forming oligonucleotides", *Nucleic Acids Research*, 22 479–484 (1994).

N. Ovsenek et al., "A maternal factor, OZ–1, activates embryonic transcription of the *Xenopus Iaevis* GS17 gene", *Development*, 115 649–655 (1992).

K.S. Prickett et al., "A Calcium–Dependent Antibody for Identification and Purification of Recombinant Proteins", *BioTechniques*, 7 580–589 (1989).

P. Rajagopal et al., "Triple–strand formation in the homopurine–homophrimidine DNA oligonucleotides $d(G-A)_4$ and $d(T-C)_4$", *Nature*, 339 637–640 (1989).

M.R. Rebagliati et al., "Antisense RNA Injections in Fertilized Frog Eggs Reveal an RNA Duplex Unwinding Activity", *Cell*, 48 599–605 (1987).

J.R. Williamson et al., "Monovalent Cation–Induced Structure of Telomeric DNA: The G–Quartet Model", *Cell*, 59 871–880 (1989).

Matthews, J. et al., "Analytical Strategies for the Use of DNA Probes, " *Analytical Biochemistry*, 169(1), pp.1–25 (1988).

Murakami, A. et al., "Fluorescent–labeled oligonucleotide probes: detection of hybrid formation in solution by fluorescence polizarization spectroscopy," *Nucleic Acids Research*, 19(15), pp. 4097–4102 (1991).

Nicoloso, M. et al., "Titration of Variant DNA Sequences Differing by a Single Point–Mutation by Selective Dot–Blot Hybridization with Synthetic Oligonucleotides," *Biochemical and Biophysical Research Communication*, 159(3), pp. 1233–1241 (1989).

Fig. 1A $$O=\overset{O^-}{\underset{O}{P}}-NCH_2CH_2OCH_3 \quad O=\overset{O^-}{\underset{O}{P}}-NCH_2CH_2N(CH_2CH_3)_2$$

Methoxyethylamine Phosphoramidate (*)

N,N-Diethylethylenediamine Phosphoramidate (+)

Fig. 1B

| | | | | | |
|---|---|---|---|---|---|
| SEQ. ID. NO:1 | 5' | A G T T T T G T C C C C T C T C A G G T G T C A C A G | | | |
| SEQ. ID. NO:18 | 3' | T C A A A A C A C A G G G G A G A G T C C A C A G T C | | | |
| SEQ. ID. NO:2 | U-1 | A-A-A-A-T-A-T-A-G-G-G-A-G-A-G | | | 0% Modified |
| | N-1 | A*A-A*A-T*A-T*A-G*G-G*G-A-G*A-G | | | 44% |
| | N-2 | A*A-A*A-T*A-T*A-G*G*G-G*A-G*A*G | | | 69% |
| | P-1 | A+A-A+A-T+A-T+A-G+G-G+G-A-G+A+G | | | 56% |
| | P-2 | A+A A+A+T-A+T+A-G+G+G-G+G-A-G+A+G | | | 69% |
| | P-3 | A+A+A+A+T+A+T+A-G+G+G-G+G-A-G+A+G | | | 88% |
| | P-4 | A+A+A+A+T+A+T+A+G+G+G+G+G+A+G+A+G | | | 100% |
| SEQ. ID. NO:3 | 5' | G C C C C C T G G C C C C C T T T G T T C C A T T T | | | |
| SEQ. ID. NO:19 | 3' | C G G G G G A C C G G G G G A A A C A A G G T A A A | | | |

SEQUENCE LISTING

<160> NUMBER OF SEQ ID NOS: 28

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 1
agttttgtgt cccctctca ggtgtcacag                                   30

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 2
aaaatatagg gggagag                                                17

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 3 gcccctggc ccctcccctt tgttccattt                                   30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4
agttttgtgt cccctctca ggtgtcacag                                   30

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 5
aaaatatagg gggagag                                                17

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6
agttttgtgt ccgcctctca ggtgtcacag        30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 7
agttttgtgt cggcctctca ggtgtcacag        30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 8
agttttgtgt cgggctctca ggtgtcacag        30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9
agttttgtgt cggggtctca ggtgtcacag        30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10
agtttggtgt cccctctca ggtgtcacag        30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 11
agttgggtgt ccccctctca ggtgtcacag        30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 12
agtggggtgt cccctctca ggtgtcacag                               30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 13
aggggggtgt cccctctca ggtgtcacag                               30

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 14
aggaggagga gatgaggagg g                                       21

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 15
agggagggag gtaagaaaaa ggg                                     23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 16
gggaaaaaga atggagggag gga                                     23

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 17
ggaataaagg ggagggg                                            17

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 18
ctgtgacacc tgagaggggg acacaaaact                              30

```
<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 19
aaatggaaca aaggggaggg gccaggggc                                30

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 20
ctgtgacacc tgagagggggg acacaaaact                              30

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 21
ctgtgacacc tgagaggcgg acacaaaact                               30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 22
ctgtgacacc tgagaggccg acacaaaact                               30

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 23
ctgtgacacc tgagagcccg acacaaaact                               30

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 24
ctgtgacacc tgagaccccg acacaaaact                               30
```

```
<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 25
ctgtgacacc tgagaggggg acaccaaact                                            30

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 26
ctgtgacacc tgagaggggg acacccaact                                            30

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 27
ctgtgacacc tgagaggggg acaccccact                                            30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 28
ctgtgacacc tgagaggggg acaccccct                                             30
```

US 6,331,617 B1

POSITIVELY CHARGED OLIGONUCLEOTIDES AS REGULATORS OF GENE EXPRESSION

CONTINUING APPLICATION DATA

This application is a continuation-in-part of parent application Ser. No. 08/619,301, filed Mar. 21, 1996 which issued as U.S. Pat. No. 5,734,040 on Mar. 31, 1998.

GOVERNMENT FUNDING

This work was performed, in part, by funding from the National Institutes of Health Grant No. HLA 42266, the government may have certain rights to this invention.

FIELD OF THE INVENTION

This invention relates to oligonucleotides used to control gene expression or other cellular events. In particular this invention relates to oligonucleotides with cationic phosphoramidate internucleoside linkages.

BACKGROUND OF THE INVENTION

Synthetic oligonucleotides have been shown to regulate gene expression in cells. Thus, these molecules bind to target regions of nucleic acids and inhibit gene expression. They are useful to control infectious disease and have been used and tested in a variety of diseases or conditions associated with altered or aberrant gene expression such as cancers, hereditary disorders, and the like.

There are two major oligonucleotide (ODN) based strategies designed to inhibit gene expression. One method uses antisense ODNs complementary to a specific mRNA to form DNA:RNA hybrids. These hybrids are stabilized by Watson-Crick base pairing and are substrates for cellular ribonuclease H (RNase H), an enzyme that degrades the RNA portion of the duplex rendering the mRNA untranslatable (Walder, et al., *Proc. Natl. Acad. Sci. USA*, 85:5011–5015, 1988). Because RNase H does not degrade the ODN, the ODN is able to hybridize to another copy of the target mRNA. Modified oligonucleotides have been disclosed for duplex-forming oligonucleotides and in one example, Letsinger et al. disclose the use of N,N,N'-trimethylethylenediamine or 4-(2 aminoethyl)morpholine internucleoside linkages to promote duplex formation (*J. Am. Chem. Soc.* 110;4470–4471, 1988)

A second ODN-based strategy for altering gene expression targets DNA by the formation of a triple helical structure. The use of ODNs to form triple helix structures was initially reported by Moser, et al. (*Science*, 238:645–650, 1987, and see LeDoan, et al., *Nucl. Acids Res.*, 15:7749–7760, 1987). Under suitable conditions, an ODN will bind in the major groove of a DNA duplex. The presence of a third strand may either sterically block transcription, prevent the sequence specific interactions of regulatory proteins with DNA, and/or alter the conformation of the bound duplex.

There are two known triplex binding motifs, both involving interactions between the bases of a relatively short ODN (generally between 11–50 base pairs) and the purine bases of a polypurine:polypyrimidine stretch of duplex DNA. In the pyrimidine motif, thymidine residues in the third strand interact with adenosine residues of an A:T duplex while a protonated cytidine in the third strand is hydrogen-bonded to the guanosine of a G:C duplex (Moser, et al., supra). The protonation of C residues at nitrogen position number three generally requires a pH less than six, and thus limits the use of this strategy in vivo (Rajagopal, P., et al., *Nature*, 339:637–640, 1989, and Lyamichev, et al., *Nucl. Acids Res.*, 16:2165–2178, 1988) unless deoxycytidine analogues are used (see Krawczyk, et al., *Proc. Natl. Acad. Sci. (ISA)*, 89:3761–3764, 1992).

The second triplex motif involves a purine rich triplex forming oligonucleotide (TFO). Thymidine or adenosine residues of the third strand bind to the adenosine of an A:T duplex and guanosine in the third strand interacts with the guanosine of a G:C duplex (Beal, et al., *Science*, 251:1360–1363, 1991, Durland, et al., *Biochem.*, 30:9246–9255, 1955, and Cooney, et al., *Science*, 241:456–459, 1988). The orientation of the third strand has been shown to be antiparallel to the purine-rich strand of the duplex (Beal, et al., supra). The major drawback to using this approach in vivo is the tendency of G-rich ODNs to self-associate into quartets at physiologic potassium concentrations. However, recent studies indicate that the use of a GT rich ODN to affect transcription of a transfected CAT plasmid in vivo indicates that GT rich combinations may minimize quartet formation. Unmodified negatively charged oligonucleotides do not generally stably participate in triplex formation in cells. Triplex forming oligonucleotide strategies must account for the physiologic concentrations of $Mg^{+2}$ and the level of potassium tolerated for stable triplex formation.

To improve the stability and cellular uptake of oligonucleotides, oligonucleotides have been prepared having modifications to the phosphate backbone. For example, phosphorothiate and methylphosphonate derivatives of oligonucleotides have been synthesized and have sequence specificity and hybridize similarly to that of unmodified oligonucleotides. Aminoethyl phosphonate derivatives of oligonucleotides have also been synthesized and demonstrate enhanced stability in aqueous solution as compared with aminoethyl phosphonate linkages (Fathi, et al., *Nucl. Acids Res.*, 22:5416–5424, 1994). The uncharged character of the methylphosphonate derivatives permits an enhanced uptake of the oligonucleotides by the cell and increased resistance to nucleases as compared with unmodified oligonucleotides. Methoxyethyl-phosphoramidate linkages have been incorporated into the internucleoside backbone at 3' and 5' linkages to inhibit exonuclease degradation. The synthesis of ODNs with some modified and some unmodified linkages allowed both increased nuclease resistance while maintaining RNase H mediated target RNA degradation. (Dagle, et al., *Antisense Res. and Devel.*, 1:11–20, 1991).

Intercalating agents have also been conjugated to oligonucleotides to increase the stability of the conjugate with the complementary strand (see, for example, Wilson, et al., *Biochem.*, 32:10614–10621, 1993, and Orson, et al., *Nucl. Acids Res.*, 22:479–484, 1994). In addition, molecules are often attached to the oligonucleotides to modify the net charge. Examples of these agents include polylysine, cationic peptides, polyamines and polycationic polymers. Intercalators and polylysine have shown an increased resistance to nuclease degradation.

Nucleomonomers can also be modified to improve triplex formation and PCT International Publication No. WO 94/24144 discloses oligomers with 7-deaza-7-substituted purines.

The formation of a DNA triplex using a purine rich ODN is inhibited by monovalent cations, particularly potassium ions (Olivas, et al., *Biochem.*, 34:278–284, 1995). Intracellular $K^+$ concentrations inhibit triplex formation using unmodified oligonucleotides. Potassium ions are the predominant intracellular cations. One problem with forming triplexes at physiologic $K^+$ levels is the self-association of guanosine-rich ODNs into aggregates which are stabilized by guanine quartets (Olivas, et al., *Biochem.*, 34:278–284, 1995; Olivas, et al., *Nucl. Acids Res.*, 23:1936–1941, 1995). In addition to decreasing the rate of triplex association, $K^+$ increases the rate of triplex disassociation in vitro (Olivas, *Biochem.*, supra). The inhibitory effect of $K^+$ can be partially diminished by chemical modification of ODNs. For example, incorporation of the modified base 6-thioguanine in place of native guanine into TFOs decreases the association of ODNs into quartets and increases triplex formation in the presence of monovalent cations (Olivas, *Nucl. Acids Res.*, supra, and Rao, et al., *Biochem.*, 34:765–772, 1995).

Another hurdle associated with the use of ODNs in vivo is that the oligonucleotides are rapidly degraded by intracellular nucleases (Rebagliate, et al., *Cell*, 48:599–605, 1987; Dagle et al., *Nucl. Acids Res.*, 18:4751–4757, 1990; Dagle, et al., *Antisense Res. and Dev.*, 1:11–20, 1991). The chemical modification of ODNs provides resistance to nucleolytic degradation (Dagle, et al., supra), potentially increasing the overall activity of these compounds in vivo (Dagle, et al., supra, and Weeks, et al., *Development*, 111:1173–1178, 1991). The type and degree of chemical modification of ODNs, however, is limited when strategies require the action of cellular RNase H (Dagle, et al., *Antisense*, supra). Additionally, some modification of ODNs can result in nonspecific toxicity mediated through non-nucleic acid interactions, such as has recently been reported for phosphorothioate ODNs and the basic fibroblast growth factor receptor (Guvakova, et al., *J. Biol. Chem.*, 270:2620–2627, 1995). In contrast, the formation of triplex structures does not require an enzymatic activity and thus allows greater flexibility with regard to ODN design. The enhanced nucleolytic stability of an ODN with some or all internucleoside linkages modified would be useful for in vivo applications if these compounds are able to form stable triplex structures. The present invention discloses a class of oligonucleotides with enhanced stability for triplex formation.

Candidate oligonucleotides should produce triplex formation at physiologic salt concentrations. The close association of two nucleic acid strands creates a highly negatively charged environment. Many oligonucleotides disclosed in the literature to date require the presence of magnesium ions above physiologic concentrations to produce stable triplex formation. The obligate presence of magnesium ions for triplex association most likely reduces interstrand charge repulsions. However, magnesium concentrations within the cell cannot be altered without altering cell physiology. Therefore, oligonucleotides dependent on minimum concentrations of magnesium ions may not function well in the cellular milieu.

The present invention discloses a class of oligonucleotides that strongly enhance triplex formation even in the presence of $K^+$ ion concentrations exceeding physiologic levels. This invention promotes oligonucleotide-mediated duplex formation and can be used for antisense technologies.

SUMMARY OF THE INVENTION

The present invention relates to the selection, production, and use of oligonucleotides with cationic phosphoramidate modified internucleoside linkages to form stable triplex DNA structures to inhibit gene expression.

In one aspect of this invention, the invention relates to a triplex-forming oligonucleotide comprising about 30% to about 100% cationic alkylpolyamine internucleoside linkages. In a preferred embodiment, the oligonucleotide comprises alkylpolyamine phosphoramidate internucleoside linkages, preferably dimethylamino propylamine linkages, N, N-diamino propylamine linkages, or diethyethylinediamine linkages. In another embodiment, the triplex forming oligonucleotide is also a duplex forming oligonucleotide and preferably the duplex forming oligonucleotide comprises ethylenediamine linkages and mixed chirality dimethylamino propylamine linkages, diethylethylenediamine linkages and not N,N,N'-trimethylethylenediamine or 4-(2aminoethyl) morpholine linkages. Preferred examples of etylenediamine-class linkages include N-ethylethylenediamine phosphoramidate internucleoside linkages or N, N-diethylethylenediamine phosphoramidate internucleoside linkages. Preferably the oligonucleotides are at least 12 nucleotides in length and in one embodiment, the oligonucleotides include at least one other modified internucleoside linkage. The oligonucleotides can further comprise a tag and preferred tags include enzymatic tags, radiolabeled tags and fluorescent tags. In a preferred embodiment, the oligonucleotides with cationic alkylpolyamine internucleoside linkages comprise at least one ethylenediamine phosphoramidate internucleoside linkage and in one embodiment, at least one diethylethyleneamine phosphoramidate internucleoside linkage.

In another aspect of this invention, the invention relates to an oligonucleotide comprising at least about 30% cationic phosphoramidate internucleoside linkages and at least about 4 bases with RNase H sensitive internucleoside linkages positioned between the cationic phosphoramidate internucleoside linkages. In one embodiment, the oligonucleotide includes at least about 6 bases with RNase H sensitive intemucleoside linkages positioned between the cationic phosphoramidate internucleoside linkages and in another embodiment, there are at least about 4 bases with cationic phosphoramidate internucleoside linkages positioned at a 5' end of the oligonucleotide and at least about 4 bases with cationic phosphoramidate intemucleoside linkages positioned at a 3' end of the oligonucleotide.

The invention also relates to a method for cleaving an RNA molecule comprising the steps of: contacting an RNA molecule in a cell with an oligonucleotide comprising at least about 30% cationic phosphoramidate internucleoside linkages and at least about 4 bases with RNase H sensitive internucleoside linkages positioned between the cationic phosphoramidate intemucleoside linkages.

In another aspect of this invention, the invention relates to a method for binding an oligonucleotide to a nucleic acid polymer comprising the steps of: preparing an oligonueleotide comprising at least one cationic alkylpolyamine internucleoside linkage; and contacting the oligonucleotide with the nucleic acid polymer. In one embodiment the nucleic acid polymer is RNA or DNA and in another embodiment the nucleic acid polymer is double stranded or single stranded. In another embodiment the method further includes the step of denaturing the nucleic acid polymer. Preferred denaturing steps include exposing the nucleic acid polymer to heat, a denaturing concentration of salt, or a chaotropic agent. In one embodiment, the nucleic acid is DNA and the contacting step forms a triplex and in another embodiment, the nucleic acid is RNA and the contacting step forms a duplex. In a preferred embodiment, the method further includes the step of introducing the oligonucleotide into a cell.

The invention also relates to a method for limiting transcription from a gene including the steps of: preparing an oligonucleotide comprising at least one cationic alkylpolyamine internucleoside linkage and capable of specifically hybridizing to at least a portion of a gene; and contacting the oligonucleotide with double stranded DNA comprising the gene, wherein the oligonucleotide binds to at least a portion of the gene to reduce the level of RNA production from the gene. In a preferred embodiment of this aspect of the invention, the oligonucleotide binds to a region of the gene selected from the group of an open reading frame, a promoter or an enhancer. In one embodiment, the oligonucleotide comprises alkylpolyamine phosphoramidate internucleoside linkages and preferably dimethylamino propylamine linkages, N, N-diamino propylamine linkages, or diethylethylemediamine linkages. In a preferred method, the method includes the step of introducing the oligonucleotide into a cell and preferred methods for introducing the oligonucleotide into a cell are known in the art and include, but are not limited to microinjection and lipid-mediated introduction.

FIGURES

FIG. 1A details structures of some of the phosphoramidate modified internucleoside linkages compared in this invention. The neutral 2-methoxyethylamine derivative on the left and the N,N-diethyl-ethylenediamine derivative (shown in an uncharged state) on the right.

FIG. 1B lists the oligonucleotides used to form triplex structures of this invention. ODNs U-1, N-1, N-2, P-1, P-2, P-3 and P-4 bind in the major groove of Duplex I,(SEQ ID NO:1) as shown. All of the triplex forming oligonucleotides (TFOs) i.e. U-1, N-1, N-2, P-1, P-2, P-3 and P-4, have the same sequence (SEQ ID NO:2) but are modified as follows: —=phosphodiester linkages, *=2-methoxyethylamine phosphoramidate linkages and +=N,N-diethyl-ethylenediamine phosphoramidate linkages. The percent of modified bonds are listed to the right of each ODN. Duplex II (SEQ ID NO:3) represents an unrelated, nontarget polypurine:polypyrimidine duplex.

DETAILED DESCRIPTION OF THE INVENTION

Figure 2:
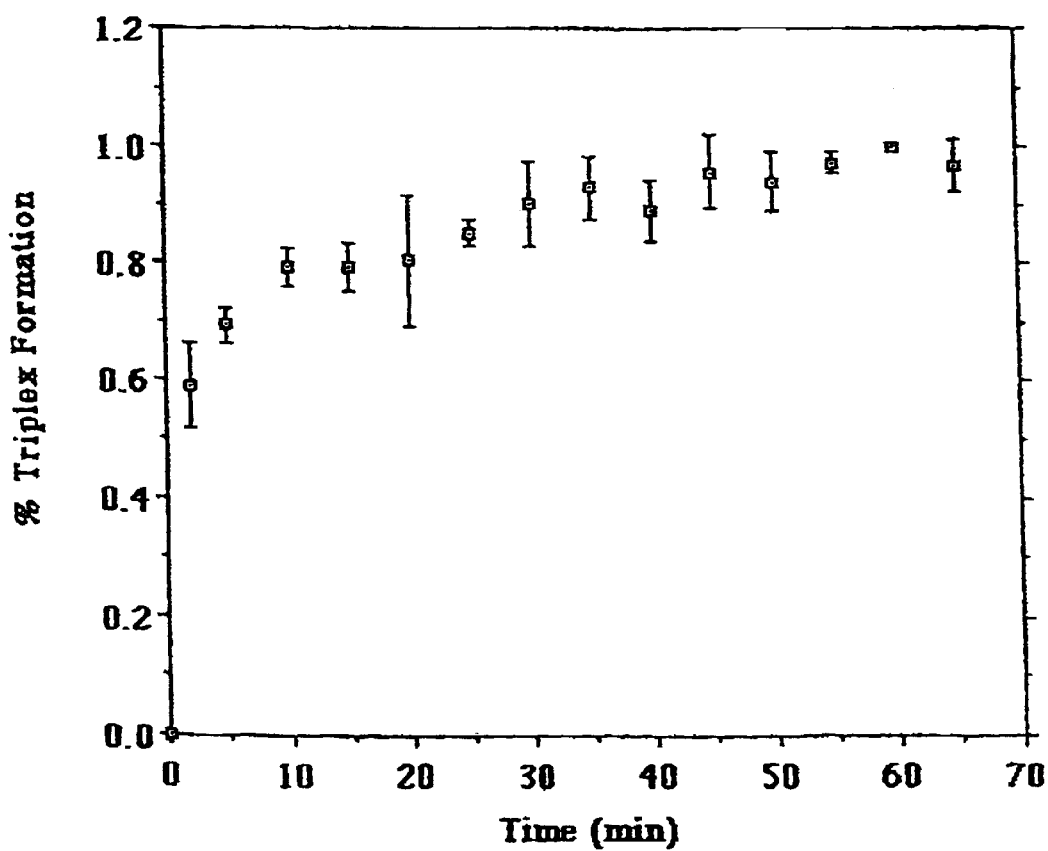
FIG. 2 is a graph demonstrating the velocity of triplex formation over time.

The present invention relates to the selection, production, and use of oligonucleotides with cationic phosphoramidate modified internucleoside linkages to form stable duplex or triplex DNA structures. The oligonucleotides can be used in a variety of ways but are particularly suited to binding nucleic acid in the cellular milieu and therefore be used to inhibit gene expression. The oligonucleotides of this invention, that is oligonucleotides with cationic phosphoramidate modified internucleoside linkages, can be prepared to bind to a variety of single-stranded or double-stranded nucleic acids and therefore have a wide range of applications for inhibiting transcription and/or translation.

The term "in vitro" is used herein to cell-free experiments (i.e., either as a cell lysate or in solution). The term "in vivo" refers to intracellular events, experiments or work performed on intact cells. That is, those of ordinary skill in this art will recognize that whether or not a particular cell is existing in culture, ex vivo, or in situ (i.e., within a particular tissue or as part of an organism), the ability of the oligonucleotides of this invention to bind to target DNA within a cell is independent of the location of the cell.

For example, transcription level-altering oligonucleotide-directed strategies can be and have been directed to a variety of cancers due to inappropriate gene activation, including leukemias (such as the use of oligonucleotides to purge bone marrow cells of leukemic progenitors prior to bone marrow transplantation) or cancers associated with oncogene activation. These types of strategies can benefit from the oligonucleotides of this invention. The oligonucleotides of this invention can also be used to control or limit viral infection (including, but not limited to, HIV, members of the Herpesvirus family including HSV, CMV, or VZV, as well as other viruses where transcription is directed from duplex DNA.) or other intracellular pathogens through the suppression, alteration, or reduction of gene expression (for a general discussion see Askari, et al., *New Engl. J. Med.*, 334(5):316–318, 1996). These oligonucleotides can also be used in duplex-forming or triplex-forming strategies for a variety of metabolic diseases including inborn errors of metabolism, hypertension, and cardiovascular disease (such as oligonucleotides engineered to inhibit cellular proliferation to prevent restenosis due to cellular hyperplasia).

As a first step in practicing this invention, target DNA of RNA is selected. The oligonucleotides of this invention are designed to specifically hybridize to a portion of a gene. The term "specifically hybridize" refers to the ability of the oligonucleotide to recognize its designed target nucleic acid while not binding substantially to non-target nucleic acid. Hybridization and wash conditions that test specific hybridization are known in the art and the Examples demonstrate methods for determining specific hybridization. In one embodiment, the target DNA for duplex or triplex formation is selected from the regulatory region of a gene whose expression is targeted for depletion. The particular target regions can come from any of a variety of regulatory regions within the DNA including, but not limited to, the promoter, the transcriptional start site or 5' of the transcriptional start site, enhancers, promoters or 5' regions of the translated portion of the gene. In one embodiment, promoter regions and other regulatory regions are preferred and methods for identifying the promoter region of a particular gene are known in the art.

Currently, regions appropriate for triplex formation require the identification of consecutive purines on one strand in a region that overlaps or encompasses the binding site for a protein:DNA complex. The mechanism of action in this case depends upon competition for the same hydrogen binding sites found in the major groove. This region is preferably upstream from the translational start site. In general, the longer the stretch of purines, the more stable the complex and the better the binding of the oligonucleotide. Our in vitro evidence suggests that a duplex region of at least 14 base pairs with two pyrimidine interruptions on the purine rich strand is sufficient for triplex formation (see Example 1). In contrast, as is well known in the art, rules for selecting oligonucleotides for duplex formation rely on Watson Crick base-pairing.

Where the target site is within a promoter, formation of a triplex in that promoter region adjacent to a protein binding region can also disrupt binding; therefore, sites around the DNA:protein interaction domains are also suitable target sites (for example, see Maher, et al., (1991), "Inhibition of DNA/protein Interactions," in *Prospects for Nucleic Acid*

*Therapy of Cancer and AIDS*, pp. 227–242, Wiley Liss, Inc.). The effect of binding of the oligonucleotide to a target region within a promoter could interfere with the proper association of the promoter and transcriptional activators. When a specific target sequence is available for binding to protein it is likely that it will also allow binding to an oligonucleotide.

A second way that duplex or triple helix formation could inhibit gene expression is to act as a physical block to the transit of the polymerase complex. The target area in this case is positioned after the transcriptional start site. There are in vitro examples of triplexes serving as physical blocks to transcription.

A third way that triplexes might disrupt transcription is by introducing structural changes that affect the ability of the polymerase complex to initiate transcription, thus, targeting areas upstream but close to the transcription initiation site may allow testing of this type of transcription initiation.

The more that is known about a regulatory region, the better the chance of altering gene expression. There are well studied examples of known binding sites for activator proteins and the sequence of the binding site can conform to the definition of purine rich (at least 13 out of 17 purines in a stretch of 17 nucleotides). The term GA rich refers to at least 10 of the 17 purines being either G or A. This sequence may be part of an enhancer or adjacent to a known protein binding domain. When little is known about the regulation of the gene, any purine stretch is a potential target that can be tested using the exemplary methods disclosed in the examples and adapted to any of a variety of target duplex DNA sequences and potential triplex forming oligonucleotides.

Methods for sequencing a particular gene or the upstream regulatory regions of a gene are known in the art; therefore, these methods will not be detailed here. Once the 5' start site and/or regulatory regions of the gene are identified, this region is sequenced and reviewed. A target region of preferably between 15–100 nucleotides of double stranded DNA is selected and more preferably a region of between 15–50 nucleotides of double stranded DNA is selected. One or more oligonucleotides are designed to bind to one or more regions of the target double stranded DNA.

The sequence of the oligonucleotide will depend on the sequence of the targeted nucleic acid. While sequences of purines are preferred for triplex formation using unmodified nucleoside bases, oligonucleotides having, for example, $N^3$-protonated deoxycytidine modifications can be used to make pyrimidine based triplex forming oligonucleotides that escape pH dependent binding to DNA duplexes (Karwczk, et al., supra). It is believed that base modifications to accommodate triplex formation by pyrimidine triplex forming oligonucleotides can be combined with the cationic phosphoramidates of this invention and that such modifications can be made and tested in view of this disclosure without undue experimentation. All duplex forming and triplex forming oligonucleotides are expected to benefit from the stability imparted by the cationic phosphoramidate internucleoside linkages of this invention.

The purine triplex motif adenosine bases in the target duplex can interact with either A or T residues. The TFOs (triplex forming oligonucleotides) in this invention are designed to be GA rich rather than GT rich, although either motif will benefit from the use of the cationic backbone modifications of this invention. The T residues in a GT rich ODN may encourage intracellular guanine quartet formation by providing points of stable hairpins. This idea is supported by examining human telomeres, structures known to form G quartets (Williamson, et al., *Cell*, 59:871–880, 1989). Human telomeres contain numerous repeats of the sequence TTAGGG, exhibiting an enhancement of T residues and a paucity of A residues.

Among the trials that serve to predict efficacy for triplex forming oligonucleotides are a series of in vitro trials using the targeted duplex and purine motif triplex forming oligonucleotides. As one way of identifying preferred oligonucleotides and as disclosed in Example 5, apparent binding constants for each triplex forming oligonucleotide may be determined and the triplex forming oligonucleotide with the best binding is used for in vitro and in vivo analysis of transcriptional inhibition.

The length of the oligonucleotide can vary. Preferably, the oligonucleotides are from about 12 bases in length to about 50 bases in length with a most preferable length of about 15 bases to about 50 bases, preferably about 15 bases to about 30 bases and still more preferably of about 15 bases to about 24 bases.

Once the sequence of the oligonucleotide has been designed or selected, the oligonucleotide can be synthesized. There are a variety of methods known in the art for synthesizing oligonucleotides. Most notably, oligonucleotides can be synthesized manually or using automated DNA synthesizers employing H-phosphonate monomers and chemistry. These methods are known in the art and for that reason will not be detailed here. The oligonucleotides of this invention incorporate modified internucleoside linkages. Cationic phosphoramidates are used to replace at least one phosphodiester linkage. Preferably the cationic phosphoramidates are cationic alkyl-polyamine phosphoramidate internucleoside linkages such as ethylenediamine-type internucleoside linkages. In a preferred embodiment, the cationic alkyl-polyamine phosphoramidate internucleoside linkages are N,N-diethyl-ethylenediamine internucleoside linkages; however, other classes of ethylenediamines are also contemplated in this invention, including, but not limited to, ethylenediamine-type linkages, including diethyl amines such as N-ethyl-ethylenediamine as well as diethyl-ethylenediamine linkages. For triplex formation, results have also demonstrated that 3-dimethylamino propylamine linkages can also be used, particularly 3-dimethylamino propylamine linkages with preferably 3 or more consecutive modified linkages. Other cationic phosphoramidates include mixed chirality propyl amines such as N, N-diamino propylamine internucleoside linkages. Preferably, the dimethylamino propylamine internucleoside linkages have at least 50% modified internucleoside linkages. Essentially, any compound that can be added by oxidative amidation to form cationic internucleoside linkages can be tested using the guidelines provided in this disclosure. Other cationic phosphoramidates suitable as substitutes for phosphodiester internucleoside linkages include, but are not limited to, diaminobutane and polylysine. Those of ordinary skill in the art of modified oligonucleotide synthesis and use will recognize that different modifications can provide advantages to oligonucleotide purification or delivery of the oligonucleotides to the cell.

This invention incorporates cationic phosphoramidate linkages during oligonucleotide synthesis. Oligonucleotides can be prepared with a single cationic phosphoramidate internucleoside linkage, or up to 100% of the internucleoside linkages can be prepared using cationic phosphoramidates. In a preferred embodiment, the range of substituted linkages is at least one modified internucleoside linkage and preferably from about 30–100% modified linkages and in another particularly preferred embodiment, the range is from about 60–100% cationic phosphoramidate substituted linkages. Preferably, the number of cationic phosphoramidate internucleoside linkages is sufficient to impart an overall positive charge to the oligonucleotide.

Example 1 details a preferred method for preparing oligonucleotides with cationic phosphoramidate linkages, where the cationic phosphoramidate is N,N-diethyl-ethylenediamine. Since the class of cationic phosphoramidates of this invention are used to create internucleoside linkages by oxidative amidation, the chemistry for synthesizing oligonucleotides using other cationic phosphoramidates will not differ significantly and those skilled in the art of oligonucleotide modifications will be readily able to prepare a variety of other oligonucleotides with other cationic phosphoramidate linkages without undue experimentation.

A number of oligonucleotides were prepared that varied in the amount of cationic phosphoramidate internucleoside linkages, as illustrated in FIG. 1. Oligonucleotides with these modified cationic linkages were compared to oligonucleotides containing neutral linkages. FIG. 1A illustrates the structure of a preferred cationic phosphoramidate modification used in this study. The methoxyethylamine derivative was used to generate oligonucleotides with neutral internucleoside linkages. Solubility of the derivative was enhanced through hydrogen bonding between water and the ether oxygen. The N,N-diethylethylenediamine derivative is shown uncharged but is protonated (and, hence, positively charged) at physiologic pH.

In one example of this invention, the sequence of the target region was derived from the enhancer of the GS17 gene of *Xenopus laevis* (Ovsenek, et al., *Development*, 115:649–655, 1992). Duplex I (SEQ ID NO:1) is 30 bp in length and contains a 17 bp purine rich region. The presence of pyrimidines on the purine rich strand makes this region an imperfect triplex forming consensus sequence but likely represents a more commonly available target than the 25–35 bp target region within the myc gene containing an uninterrupted polypurine:polypyrimidine sequence that is often used for in vitro studies.

The ODNs used in one example in this study are identical in nucleic acid sequence and correspond to SEQ ID NO:2. Each oligonucleotide illustrated in FIG. 1B contains either no modifications (oligo U-1), neutral internucleoside linkages (N-1 and N-2), or cationic phosphoramidate internucleoside linkages (P-1 through P-4). In designing the oligonucleotides, thymidine was chosen to interact with the 2 C:G inversions based on a report demonstrating significant T.C:G binding (Durland, et al., *Nucleic Acids Research*, 22:3233–3240, 1994). N-1 and N-2 represent identical oligonucleotides containing 7 and 11 neutral methoxyethyl phosphoramidate linkages, respectively. These neutral bonds are represented by * in FIG. 1. ODNs P-1 through P-4 contain increasing numbers of positively-charged N,N-diethyl-ethylenediamine phosphoramidate linkages, from 9 to 16. The positive linkages are represented as + in FIG. 1. The extent of modification of each ODN is indicated to the right of the sequence.

The positive internucleoside linkage was made by amidation of the corresponding hydrogen phosphonate diester with N,N-diethyl-ethylenediamine as described in Example 1. N,N-diethyl-ethylenediamine is a preferred example of the type of molecule that can be used for successful cationic modification. The primary and tertiary amine moieties allow for a more specific reaction and minimize oxidative amidation at each end of the diamine. Oxidative amidation has the potential for crosslinking oligonucleotides. Moreover, the pKa of a tertiary amine is higher than that of the corresponding primary or secondary amine. The resulting increased degree of protonation of the ODN produces a greater net positive charge at physiologic pH.

Once target nucleic acid has been identified and oligonucleotides are synthesized, synthetic target nucleic acid can be prepared to test the ability of the synthesized oligonucleotides to bind to the target nucleic acid under physiologic conditions. The oligonucleotides provided in FIG. 1 were tested in vitro and the ability of the oligonucleotides containing neutral internucleoside linkages to form triplex structures was compared to the triplex forming ability of oligonucleotides with cationic phosphoramidate substituted linkages. Example 3 details methods for testing triplex formation in vitro using both negatively charged, neutral, and positively charged oligonucleotides.

Experiments were performed to test for the ability of a particular modified oligonucleotide to bind to duplex DNA. Example 4 details the results of binding studies to assess triplex formation between an unmodified negatively charged oligonucleotide and oligonucleotides N-1 and N-2, where negative charges were replaced with uncharged phosphoramidates. These experiments were performed in mM $Mg^{2+}$ without potassium with ODN concentrations ranging from 20 nM to 2 $\mu$M. Triplex formation was found to be more efficient as negative phosphodiester linkages were converted to neutral phosphoramidate derivatives. Without limiting the scope of this invention, the most likely explanation for this observation is that the oligonucleotides containing the uncharged phosphoramidates carry a significant net negative charge and are repulsed, although less than unmodified oligonucleotide U-1, by the negative charge density of Duplex I (SEQ ID NO:1).

The requirement for relatively high concentrations of $Mg^{2+}$ in order to form triplex DNA using the neutrally modified ODNs supports the hypothesis that charge remains a major factor affecting triple strand association. Increases in triplex formation can result from either increased affinity for the DNA duplex or decreased tendency toward formation of guanine quartets. The latter could increase the effective concentration of the TFO. Any ODN modification, whether directed at the bases, the sugar moiety, or the phosphate backbone, has the potential to affect either or both of these equilibria.

In contrast to the oligonucleotides containing neutral modifications, nearly complete conversion of duplex DNA to triplex DNA was observed with the cationic phosphoramidates tested (see Example 5). The formation of triplex DNA in the presence of $K^+$ is important in determining whether the cationic phosphoramidates of this invention are useful in vivo. Example 6 details the effect of potassium chloride on triplex formation using the cationic phosphoramidates of this invention. The cationic phosphoramidate substituted oligonucleotides were significantly better at forming triplex structures than their unmodified or neutral counterpart. Moreover, increasing the amount of cationic internucleoside linkages increased the amount of triplex formation.

Triplex formation in the presence of LiCl, NaCl, and KCl was evaluated to determine whether the observed triplex inhibition was potassium-specific or resulted from increases in the ionic strength of the solution. Example 7 discloses methods for assessing the effect of various monovalent cations at concentrations of 40 mM, 80 mM, and 120 mM on triplex formation. Triplex formation was at least affected by increasing concentrations of LiCl. NaCl caused an intermediate level of inhibition and KCl had the greatest effect on triplex formation.

The effect of extensive cationic phosphoramidate modification on triplex formation was examined with oligonucleotides containing 88% modified linkages and 100% modified linkages (see Example 8). The ability of these oligonucleotides to associate with target duplex DNA was compared to unmodified oligonucleotides with the same base sequence at 130 mM $K^+$ and 1 mM $Mg^{2+}$, concentrations that approach physiologic salt concentrations. Oligonucleotides with extensive cationic phosphoramidate linkage modification demonstrated an improved capacity to form triplex structures.

The oligonucleotides were also tested for their capacity to form triplex DNA structures under stringent salt conditions (see Example 9). Results demonstrated that triplex formation with oligonucleotides containing increasing levels of cationic phosphoramidate linkages were less sensitive to $K^+$ concentration. Unexpectedly, almost 90% of Duplex I (SEQ ID NO:1) was in the triplex form at 250 mM KCl. Increasingly positively-charged internucleoside linkages from 11 of 16 (69%) in P-2 to 14 of 16 (88%) in P-3 is associated with a significant decrease in potassium-mediated inhibition of triplex formation. In addition, and also unexpectedly, although magnesium is known to stabilize traditional triplex DNA, the results of Example 10 indicated that oligonucleotides with extensive cationic phosphoramidate modifications were essentially unaffected by $Mg^{2+}$ at physiologic $K^+$ concentrations.

This invention demonstrates that positively-charged ODNs with cationic phosphoramidate modified internucleoside linkages are significantly more effective in forming triplex DNA than the corresponding unmodified or neutrally-modified compounds. When an ODN is designed to interfere with intracellular nucleic acid metabolism, specificity becomes a crucial issue. Nonspecific electrostatic interactions between positively-charged ODNs and nontarget duplex DNA are a potential concern with these compounds. Example 11 discloses methods for testing the specificity of the oligonucleotide for its target using unmodified and cationic phosphoramidate modified oligonucleotides.

A second double stranded DNA strand nonspecific for the oligonucleotide (SEQ ID NO:3) was used to demonstrate the specificity of the oligonucleotides of this invention for their target duplex DNA. Duplex II (SEQ ID NO:3), illustrated in FIG. 1, is a random, polypurine:polypyrimidine 30 bp sequence with 5 inversions. This duplex is used to measure nonspecific binding of a positively-charged ODN to a DNA duplex and, as disclosed in the examples, is used to assess triplex forming oligonucleotide specificity. The sequence is found in the GS17 promoter, just downstream of the oligonucleotide target site. This sequence is random with respect to the selected oligonucleotides designed to bind to the GS17 promoter and can therefore be used to assess specificity for any oligonucleotide that is targeted for triplex formation at a particular duplex DNA sequence; however, those of ordinary skill in the art will also appreciate that other duplex sequences can be used to assess the binding specificity of other oligonucleotides and that it is possible to produce nonspecific duplex DNA fragments from regions near or adjacent to a given targeted duplex DNA sequence to assess nonspecific binding, as well.

To further investigate these nonspecific interactions under salt concentrations more closely resembling in vivo conditions, the experiment was repeated in 130 mM KCl. Oligonucleotides with extensive cationic phosphoramidate modifications had reduced nonspecific binding to Duplex II under physiologic concentrations of $K^+$.

The inability of purine rich ODNs to form triplex DNA in the presence of physiologic concentrations of $K^+$ is a major hurdle in the development of oligonucleotide compounds as regulators of gene expression. This invention describes a class of positively charged ODNs that can efficiently form duplexes and/or triplexes in the presence of physiologic and even supraphysiologic levels of potassium.

Replacing negative phosphodiester bonds with positively-charged phosphoramidate linkages resulted in compounds that more efficiently formed triplexes with double stranded target DNA. A progressive increase in triplex forming ability was observed with increasing positive charge. As discussed above, this was demonstrated by: (1) a decrease in $K_d$ with increasing ODN modification, (2) a decreased sensitivity to the inhibitory effects of monovalent cations on triplex formation, and (3) a diminished requirement of $Mg^{2+}$ in order to form triplex DNA. Without intending to limit the scope of this invention, because of the $Mg^{2+}$ independence of triplex association observed using oligonucleotides with at least 80% cationic phosphoramidate modified linkages, it is likely that electrostatic attraction between the ODN and the target duplex is a predominant force stabilizing the triplex. In addition to electrostatic attraction, it is possible that positively charged ODNs will have a reduced capacity to form guanine quartets and that both mechanisms could act to promote triplex formation.

A second benefit of the oligonucleotides of this invention, as compared to other modified oligonucleotides (such as phosphorothioates), is the reduced levels of nonspecific association between cationic phosphoramidate modified oligonucleotides with nontarget duplex DNA. Under physiologic levels of potassium chloride, the nonspecific binding of oligonucleotides with greater than 80% cationic phosphoramidate modification was nearly undetectable. Thus, under conditions that more closely approach physiologic, the extent of nonspecific triplex formation becomes minimal.

A third benefit of the oligonucleotides of this invention is that the cationic phosphoramidate modified internucleoside linkages, like other internucleoside modifications, are resistant to RNase activity. This resistance enhances stability of the oligonucleotide in the cell.

The cationic phosphoramidate modified oligonucleotides of this invention can additionally incorporate other oligonucleotide modifications known in the art. For example, the oligonucleotide may include base modifications including, but not limited to, 6-thioguanine base substitutions for purine:purine motif triplex forming oligonucleotides (Olivas, W. M. and Maher, L. J. III, *Nucleic Acids Res.*, 23:1936–1941, 1995, and Rao, T. S., et al., *Biochemistry*, 34:765–772, 1995). Alternatively, $N^3$ protonated deoxycytidine analogs can be incorporated into oligonucleotides for pyrimidine:purine motif triplex forming oligonucleotides (see Froehler, et al., *Nucleic Acids Res.*, 14:5399–5407, 1986). Other base modifications that could also be incorporated into the oligonucleotides of this invention include, but are not limited to, methyl cytidine and alkynyl base modifications.

In addition, the oligonucleotides can be labeled with tags or labels such as enzymatic tags, radiolabeled tags and flourescent tags including, but not limited to, fluorescein, Rhodamine Green, Rhodamine Red, Texas Red, Biotin, DNP, and the like (see, for example, FluoReporter Oligonucleotide Amine Labeling Kits provided by Molecular Probes, Eugene, Oreg.). Suitable chromophores are those with amine groups that can be added by oxidative amidation. In addition, chromophores with isothiocyanate groups can also be used. These can be added to the oligonucleotide during synthesis using oxidative amidation of H-phosphonate diester with diamine or can be reacted with available amines. Similarly, the oligonucleotides of this invention can be coupled to haptens or any of a variety of fluoroprobes that do not interfere with the binding characteristics of the modified oligonucleotides for their target DNA. These oligonucleotides can be used to monitor binding of the labeled oligonucleotide to duplex DNA.

Once the oligonucleotides have been tested for their binding affinity to target duplex DNA, the cationic phosphoramidate modified probes of this invention can be tested to determine in vivo efficacy. Deliverable concentrations of oligonucleotides can produce triplex or duplex formation. There are a variety of methods known in the art for introducing oligonucleotides into cells in culture. These methods include, but are not limited to, microinjection, liposome technology including antibody directed liposomes or antibody directed oligonucleotides as well as non-targeted liposomes and/or multi-lamellar vesicles.

As a preferred testing regime, the oligonucleotides are microinjected into cells obtained from animal or man. The cell type chosen is determined by the presence or absence of the selected target nucleic acid in the cell type. As one example, the target nucleic acid is a sequence of duplex DNA from the enhancer region of the GS17 gene of *Xenopus laevis*, corresponding to Duplex I (SEQ ID NO:1) of FIG. 1, and the oligonucleotides tested have the nucleic acid sequence and base modifications of oligonucleotides P-3 and P-4 of FIG. 1. Although embryos and oocytes from *Xenopus laevis* are used in these studies and the target duplex DNA is the GS17 gene, oligonucleotide delivery to a variety of cells in culture, ex vivo and in situ (i.e., within an animal) is known in the art and those skilled in the art will recognize the applications of these examples to a wide variety of target duplex DNA sequences resident in a variety of eukaryotic cells.

There are two factors that are assessed in determining the ability of a particular oligonucleotide to mediate an inhibitory effect on transcription; toxicity of the oligonucleotide to the cell and effect of the oligonucleotide on targeted transcriptional inhibition. Example 12 details methods for assessing the cellular toxicity of the oligonucleotide and Example 13 discusses methods for assessing the effect of the cationic phosphoramidate modified oligonucleotide on transcriptional inhibition. Reduction in transcription rates is analyzed by measuring either mRNA levels produced by the targeted genes or by assaying for levels of the protein product encoded by the mRNA. Methods for measuring both mRNA and protein production from a cell are well known in the art.

Once an inhibitory effect has been observed in vitro, it is contemplated that the oligonucleotides of this invention can be used to impart a transcriptional impact on eukaryotic cells. Thus, in one embodiment of a method for inhibiting expression of a gene in an animal, a cell sample is removed from an animal and processed to produce a cell sample that can be treated with the oligonucleotides of this invention using, for example, the methods disclosed in PCT patent application WO 9411524 to Anderson, et al. In a second embodiment, the oligonucleotides of this invention are encapsulated in lipids, using the methods and techniques disclosed in PCT published patent applications WO 9517373 to Ciccarone, et al., WO 9014074 to Abai, et al., or U.S. Pat. No. 5,194,654. The lipid/oligonucleotide formulation is delivered to the animal or human by parenteral or oral routes of administration including, but not limited to, intravenous, subcutaneous, intramuscular, mucosal introduction such as through the use of aerosols or drips, and alimentary introduction. Those skilled in the art will recognize that the choice of delivery will be determined by the source of cells containing duplex DNA targeted for gene expression inhibition.

There are complications in using oligonucleotides within the cellular milieu and these can be overcome using the oligonucleotides of this invention. Oligonucleotides can be prepared from pyrimidines, purines or a combination of both types of nucleic acids. Oligonucleotides prepared substantially using pyrimidines require an acid pH for binding, for example to the major groove of a DNA helix for triplex formation. Oligonucleotides prepared predominantly from purines have a tendency to self associate at cellular concentrations of potassium. In addition, triplex forming or duplex forming oligonucleotides with standard phosphodiester linkages are sensitive to cellular nucleases. The oligonucleotides of this invention do not have these problems because a cationic amine replaces one of the oxygens attached to the phosphate rendering the oligonucleotides resistant to nuclease activity and enhancing the ability of the purine based oligonucleotides to form triplexes rather than self-associate. Similarly, the cationic modifications would also protect pyrimidine oligonucleotides from degradation in the cell. Duplex binding data indicates that the cationic modifications produce a more stable, less salt dependent association.

Within a cell, oligonucleotide association with a DNA duplex to form a triplex must compete with proteins that also bind to the DNA. The speed that a triplex can form is a measure of the likelihood of the oligonucleotides to be able to compete within the cell. In Example 15, the formation of DNA triplex was assayed under conditions of neutral pH, 130 mM KCl and 1 mM $MgCl_2$. Results demonstrated that the rate of triplex formation was rapid (see FIG. 2). These experiments suggest, for example, that at an oligonucleotide concentration of 2 $\mu$M that half occupancy of the triplex target sites would take about 2 minutes. This approaches the time needed for histones to associate with newly synthesized DNA. Because the toxicity testing indicates that the oligonucleotide concentration can be increased in the nucleus by at least a factor of 10 without ill effects to the cell, it is anticipated that under normal cellular conditions, oligonucleotide association with triplex target can compete well against histone locking of the target site.

Formation of a triplex can compete for transcription factor binding because the same hydrogen bonds are used by transcription factors to regulate specific genes. Therefore, if the oligonucleotide can compete with a transcription factor for the same site, transcriptional activation will be inhibited. Example 16 demonstrates that oligonucleotides modified with ethylenediamine phosphoramidate internucleoside linkages can specifically compete for target site binding with a cellular transcription factor. As demonstrated in Example 16, the binding of transcription factor (OZ) shifts the mobility of its DNA duplex target on a standard gel shift assay using a signal to reflect the mobility of labeled duplex DNA. The $^{32}$P-labeled target site for the OZ transcription factor (i.e., the duplex DNA) was present at 1 ng. Addition of sequence specific oligonucleotide with ethylenediamine phosphoramidate internucleoside linkages at between 20 nM and 20 μM lead to a loss of OZ protein/DNA interaction and the appearance of oligonucleotide mediated triplex formation. Control oligonucleotides did not produce this effect indicating that the effect was sequence specific. The results indicated that in direct competition with a known DNA transcription factor (OZ), a triplex forming oligonucleotide modified with ethylenediamine-class phosphoramidate internucleoside linkages preferentially associated with duplex DNA.

The formation of a triplex in the transcribed portion of a gene can serve as a roadblock causing premature termination of RNA polymerase II and loss of the ability of the gene to direct product. This interaction does not require competition with sequence specific DNA binding proteins, rather it only requires a triplex forming consensus region (e.g., a duplex region of 15 base pairs with two pyrimidine interruptions on a purine rich strand, for purine rich targets) in the transcribed portion of a gene. Example 17 provides an example of the ex vivo expression of an SV40/CAT (chloramphenicol acetyl transferase) plasmid that is inhibited in the presence of the cationic oligonucleotides of this invention when a triplex forming target is present in the transcribed region of the CAT gene. Xenopus oocytes were injected with 1 μg of either plasmid CV or DV. The pCV has the CAT gene controlled by the SV40 early promoter while plasmid DV is the same plasmid with a triplex target site in the transcribed region of the CAT gene. Oocytes were co-injected with a plasmid transcribing β-galactosidase to assay general, non-sequence specific transcription effects. The oligonucleotide modified with ethylenediamine phosphoramidate internucleoside linkages directed to the CAT plasmid (pDV) including the triplex target site (pDV) resulted in undetectable levels of CAT activity. Therefore, the formation of an oligonucleotide-mediated triplex in the transcribed region of the gene led to gene inactivation, even when the gene had a strong viral promoter and enhancer (such as the SV40 early promoter and enhancer). The data also indicated that while the modified oligonucleotides of this invention were able to inhibit CAT gene expression, the same concentration of unmodified oligonucleotide did not inhibit CAT gene expression (see Example 17). Moreover, in vitro studies to determine the effect of oligonucleotide base sequence on triplex formation produced the anticipated regulatory effect on transcription in vivo.

The results of these studies indicate that the oligonucleotides of this invention inhibit gene expression in a sequence specific fashion. In particular, the data of Example 17 indicates that if the triplex target site is in the portion of the gene that is transcribed, the formation of a triplex results in gene inactivation.

Xenopus oocytes are a widely used and accepted model for studying cellular events. Results from intracellular studies using this model are consistent and predictive of cells in vivo and facilitate the analysis of events related to gene expression and protein production (see for example, Methods in Cell Biology vol. 36 entitled "*Xenopus laevis*: practical uses in cell and molecular biology" 1991. Academic Press. B. Kay and H. B. Peng, eds). For example, the ease of direct injection of genes with or without other molecules of interest into a single cell (the ooctye) reduces the number of variables that must be controlled for effective analysis of data. Similarly, Xenopus embryos can be injected at the one cell stage and the effect of the oligonucleotides of this invention on the expression of an endogenous gene (or alternatively, the effect of antisense strategy oligonucleotides at the mRNA level) can be examined. Results from these studies are predictive of other embryos and oocytes as well as other cells whether in culture or in an animal.

In studies relating to the present invention, an endogenous GS17 enhancer in the Xenopus oocyte was used as the target site for triplex forming cationic oligonucleotides, endogenous gene activity was reduced by one-half to one-fourth of its normal level, indicating that cationic oligonucleotides, according to this invention, have a regulatory effect on the expression of an endogenous gene (see Example 17).

In another aspect of this invention, this invention relates to the use of the oligonucleotides with cationic ethylene diamine phosphoramidate internucleoside linkages to hybridize as a duplex to DNA or RNA. Preferably the internucleoside linkages for duplex formation are not N,N, N'-trimethylethylenediamine or 4(2-aminoethyl)morpholine linkages and are preferably N-ethyl ethylenediamine or N, N-diethyl-ethylenediamine phosphoramidate internucleoside linkages. The nucleic acid can be genomic or extrachromosomal including, but not limited to, plasmids, episomes, or linear nucleic acid such as viral nucleic acid. Advantageously, the oligonucleotides of this intention are capable of hybridizing to form duplex DNA or RNA-DNA structures in the presence of chaotropic against and low salt.

Figure 3:
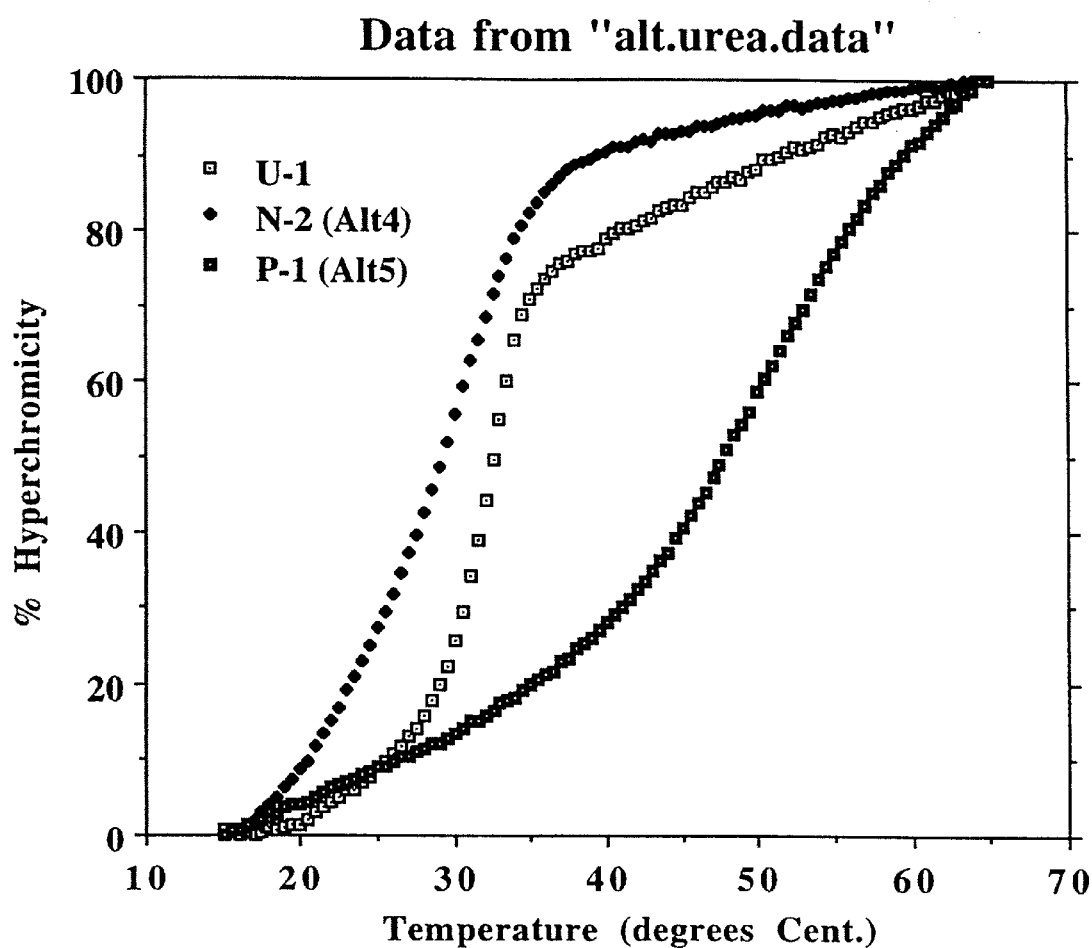
FIG. 3 is a graph demonstrating the ability of the oligonucleotides of this invention to form duplex even under DNA-DNA denaturing conditions.

In one example, using thermal denaturation studies where salt concentration was varied to analyze the stability of duplex formation using the oligonucleotides of this invention, in 150 mM NaCl, unmodified oligonucleotides and cationic oligonucleotides both had Tm's of about 50° C., however, as salt concentration was lowered to 0 mM NaCl, unmodified oligonucleotides exhibited a decreasing Tm while the oligonucleotides of this invention with 100% modified internucleoside linkages were unaffected. Thus, the formation of duplex using oligonucleotides with the internucleoside linkages of this invention formed duplexes with target nucleic acid independent of salt concentration. In a second example, the oligonucleotides of this invention can be used as probes to bind to denatured double stranded DNA or to denatured RNA. FIG. 3 provides a graph indicating that the oligonucleotides of this invention form duplex structures with nucleic acid and that advantageously the oligonucleotides of this invention can bind very strongly as a duplex, even under what would normally be considered DNA-DNA denaturing conditions. As illustrated in FIG. 3, in 500 mM urea, cationic oligonucleotides have a Tm almost 20° C. higher than unmodified oligonucleotides and the same is true for similar experiments conducted in 10% formamide.

The term "denatured nucleic acid" or "DNA-DNA denaturing conditions" is used herein to refer to conditions that promote the conversion or disassociation of nucleic acid, such as DNA or RNA from a double-stranded state (double stranded in whole or in part) into a single-stranded state. This conversion can be accomplished through a variety of methods including, but not limited to, heat, reduced salt concentrations, detergents, or the addition of chaotropic agents such as for example, formamide, urea or a guanidinium salt, and the like. The oligonucleotides of this invention can bind to nucleic acid under, for example, urea concentrations ranging from less than 0.5M urea to at least 7M urea. Exemplary testing regimes are provided in Example 18.

Advantageously, the oligonucleotides of this invention can bind to single stranded DNA or RNA, including denatured double-stranded DNA, under conditions that would not support the formation of a hybridization complex if oligonucleotides with only phosphodiester internucleoside linkages were used. The oligonucleotides of this invention that are capable of hybridizing to DNA or RNA under DNA—DNA duplex denaturing conditions comprise at least about 30% cationic phosphoramidate internucleoside linkages and preferably at least about 70% cationic phosphoramidate internucleoside linkages.

The oligonucleotides of this invention can also be used as antisense agents. Improving the stable association of an oligonucleotide with RNA and increasing the nuclease resistance of the oligonucleotide can both enhance effectiveness of the oligonucleotide in a cell and/or in the body. Oligonucleotides with neutral alkylamine phosphoramidate internucleoside linkages (such as methoxy ethylamine internucleoside linkages) can hybridize to single stranded nucleic acid (DNA or RNA) both in vitro and in vivo (see for example, Dagle et al. *Nucl. Acids Res.* 19:1805–1810, 1991; Weeks et al. Development 111:1173–1178, 1991; and Potts et al, *PNAS* (USA) 88:1516–1520, 1991). Neutral modifications slightly decreased the stability of the duplexes formed with these oligonucleotides. In contrast, oligonucleotides with cationic alkyl-polyamine phosphoramidate intemucleoside linkages (such as ethylenediamine-type linkages) increased the stability of the duplex formed (see Example 18). The thermostability of nucleic acid duplex formation (the target for duplex formation was a complementary unmodified single stranded DNA molecule) was compared using unmodified (U 1), 68% neutral alkyl-polyamine phosphoramidate internucleoside linkages, or 56% cationic alkyl-polyamine (ethylenediamine-class) phosphoramidate internucleoside linkages. The hybridization reaction was carried out in 500 mM urea and the Tm was determined by determining the percent hyperchromicity as calculated by determining the absorbance at 260 nm in a thermally controlled spectrophotometer between 15° and 70° C. Consistent with previous data, neutral alkyl-polyamine phosphoramidate internucleoside linkages formed duplexes slightly less stable than those formed with unmodified oligonucleotides. In contrast, the Tm of duplexes formed with the cationic oligonucleotides of this invention was about 15° higher than for unmodified oligonucleotides demonstrating a dramatic change in thermostability.

In a preferred embodiment of this invention the oligonucleotides for duplex formation in nucleic acid denaturing conditions preferably include at least 5 and preferably at least 6 consecutive unmodified linkages and preferably one or more modifications, including the modifications of this invention to protect the 3' end of the oligonucleotide from exonuclease activity.

In vivo data supports the ability of oligonucleotides with cationic alkyl-polyamine phosphoramidate internucleoside linkages to bind to RNA and lead to RNase mediated degradation. As mentioned earlier, although a variety of maternally inherited mRNAs have been depleted using antisense oligonucleotides, currently available modifications are unable to diminish mRNAs transcribed in the embryo.

The oligonucleotides of this invention can be used in antisense strategies. In a preferred application of an antisense strategy, the oligonucleotides of this invention include modification in the 5' terminus of the oligonucleotide with RNase H sensitive internucleoside linkages (such as naturally-occurring internucleoside linkages) as a target for RNase H cleavage.

There are a variety of RNase H sensitive internucleoside linkages that are known in the art and these include naturally occurring internucleoside linkages as well as phosphorothioate internucleoside linkages. The oligonucleotides for antisense applications can be a variety of lengths and preferably at least 12 nucleotides in length. The oligonucleotides preferably include a region of at least about 4 RNase H sensitive consecutive internucleoside linkages and preferably at least about 6 consecutive internucleoside linkages positioned between the cationic phosphoramidate internucleoside linkages of this invention.

In one example, the GS-17 transcript was targeted using a 17 mer with cationic modifications (e.g. ethylenediamine-type internucleoside linkages) at the 5' and 3' ends and 6 consecutive phosphodiester bonds to support the activity of RNase H. The oligonucleotide was injected just after fertilization of Xenopus eggs. RNA was isolated from embryos ten hours after fertilization. There was a dramatic difference between the level of GS17 mRNA in control injected and oligonucleotide injected embryos. Moreover, the response was dose dependent. As little as 10 ng of oligo resulted in greater than 90% degradation of GS17 transcript without evidence of cell toxicity. Identical treatment of embryos using oligos with neutral backbone modifications (methoxyethylamine) or phosphodiester backbones resulted in no detectable reduction of the GS17 transcript. Experiments reported by others (Woolf, et al. 1990) indicated that levels of phosphorothioate oligonucleotides sufficient to degrade even a maternal mRNA(present at the time of injection) are toxic to the embryo. Thus, oligos with cationic alkyl polyamine phosphoramidate internucleoside linkages that retain enough unmodified linkages to support RNase H mediated degradation are superior antisense reagents.

Those skilled in the art will recognize that there are a variety of modifications within the scope of this invention and that the examples that follow are exemplary and not limiting. All references cited throughout this text are herein expressly incorporated by reference.

EXAMPLE 1

Oligonucleotide Synthesis

Modified ODNs were synthesized on an ABI model 391 PCR-mate DNA synthesizer using hydrogen phosphonate chemistry (Froehler, et al., *Nucleic Acids Res.*, 14:5399–5407, 1986). All reagents used for automated DNA synthesis were obtained from Glen Research (Sterling, Va.). To generate unmodified phosphodiester bonds, hydrogen phosphonate diesters were oxidized for 4 minutes with freshly prepared 5% iodine in THF:pyridine:water (15:2:2) and then 3 minutes with the same solution diluted 1:1 with 8% TEA in THF:water (43:3). Oxidative amidation of hydrogen phosphonate diesters was performed manually using a 10% solution of either 2-methoxyethylamine or N,N-diethyl-ethylenediamine (Aldrich) in anhydrous $CCl_4$ as previously described (Dagle, et al., *Nucleic Acids Res.*, 18:4751–4757, 1990). ODNs containing both phosphodiester and phosphoramidate linkages were synthesized in blocks. The desired number of 3' residues was first coupled and then either oxidized or oxidatively amidated. The next block of residues was then individually condensed and subsequently oxidized or oxidatively amidated. Purification of ODNs was performed as described previously (Dagle, *Nucl. Acids Res.*, supra). Following Sephadex G-25 column chromatography (Pharmacia) to remove small molecular weight impurities, ODNs were dissolved in sterile water and quantitated by UV spectroscopy. It was assumed that the modified linkages did not significantly effect the extinction coefficients of the individual ODNs. ODN heterogeneity was assessed using denaturing reversed-polarity gel electrophoresis. The presence of a distinct band was indicative of a homogenous oligonucleotide population.

EXAMPLE 2

Oligonucleotide Labeling

Target duplexes are formed from a 1:1 mixture of complementary unmodified 30-mer ODNs which are heated to 80°

C. for 5 minutes and allowed to slowly cool to room temperature. These duplexes were 5' end-labeled with T4 polynucleotide kinase (Promega, Madison, Wis.) and γγ-$^{32}$P-ATP (6000 Ci/nmole, Amersham). 2 pmole of DNA duplex (4 pmole of 5' ends) was incubated at 37° C. for 45 minutes under the following conditions: 70 mM Tris pH 7.6, 1 0 mM $MgCl_2$, 5 mM DTT, 8 pmole ATP and 3 U T4 polynucleotide kinase in a total of 10 μl. The reaction was stopped by the addition of 90 μl of 7.5 M ammonium acetate and subsequent phenol:chloroform extraction. The aqueous phase was added to 20 μg of carrier glycogen. To this was added 300 μl ethanol and the solution was kept at −70° C. for at least 30 minutes. Following centrifugation, the pellet was resuspended in water to a concentration of 10 nM.

EXAMPLE 3

Triplex Formation Assay

Triplex formation was initiated by the addition (in order) of 5 ul H20, 2 μl 5×buffer (100 mM Tris-HCl pH 7.5, 0 to 50 mM $MgCl_2$), 1 μl labeled DNA duplex (2–10 femtomoles), 1 μl yeast tRNA (1 mg/ml), and 1 μl triplex forming ODN. The buffer solutions and ODN concentrations were altered to examine triplex formation under various conditions. The mixtures were incubated at ambient temperature overnight. After the addition of 1 μl of gel loading buffer (0 to 10 mM $MgCl_2$ to match the assay conditions, 20 mM Tris-HCl pH 7.5, 50% glycerol and 0.05% each bromophenol blue and xylene cyanol), the samples were loaded onto a 15% polyacrylamide (acrylamide:bisacrylamide= 100:1) gel and analyzed by nondenaturing gel electrophoresis. The electrophoresis buffer was TMB (90 mM Tris base, 90 mM boric acid, and 1 0 mM $MgCl_2$). Electrophoresis was performed at 4° C. for 4–6 hours. The gel was dried under vacuum and exposed at −70° to Kodak X-OMAT AR film using an intensifying screen. The amount of radioactivity present in the duplex and triplex forms was determined by electronic autoradiography (Instantlmager, Packard, Downers Grove, Ill.). The fraction of target duplex bound by a TFO, θ, was calculated using the equation:

$$\theta = S_{triplex}/(S_{triplex} + S_{duplex})$$

where $S_{duplex}$ and $S_{tripiex}$ represent the electronic autoradiographic signal for the duplex and triplex bands, respectively. The Kd for an ODN in triplex formation was determined from the concentration of the compound which causes ½ of the target duplex to shift to the triplex form.

EXAMPLE 4

Effect of Charge Neutralization on Triplex Formation

Negative charges were removed from the oligonucleotide of FIG. 1 and replaced with neutral charges using the methoxyethylamine derivative illustrated in FIG. 1. ODNs-1 and N-2 were compared with their unmodified counterpart, U-1, for the ability to form triplexes with Duplex I (SEQ ID NO:1). These experiments were performed in 10 mM $Mg^{2+}$ and no $K^+$, with ODN concentrations of 0 nM, 20 nM, 200 nM, and 2 μM for each of the three oligonucleotide samples. A gel shift assay was performed. Triplex formation was seen with increasing concentrations of U-1, N-1, and N-2. Triplex formation was more efficient as negative phosphodiester linkages were converted to neutral phosphoramidate derivatives. 2 μM of unmodified oligonucleotide shifted a small amount of Duplex I (SEQ ID NO:1). With decreasing negative charge, an increasing fraction of Duplex I (SEQ ID NO:1) was shifted to the more slowly migrating triplex form.

EXAMPLE 5

Triplex Formation with ODNs Containing Positively-Charged Internucleoside Linkages ODNs P-1 and P-2 were also compared to the unmodified oligonucleotide, U-1, in a gel shift assay. The assay was performed in 1 mM $MgCl_2$ and no $K^+$ and demonstrated a significant increase in triplex formation in those oligonucleotides with positively-charged internucleoside linkages. Interestingly, U-1 is unable to shift more than 15% of Duplex I to a more slowly migrating form at 2 μM, the highest ODN concentrations examined. No distinct triplex band was visible. In contrast, nearly complete conversion of duplex to a distinct triplex was observed with oligonucleotides P-3 and P-4 over the 2 nM to 2 μM concentration range tested (samples were tested at 2 nM, 20 nM, 200 nM, and 2 μM). The Kd for U-1 could not be measured under these conditions. The Kd for P-1 was about $8 \times 10^{-7}$ M, while that of P-2 was about $8 \times 10^{-8}$ M.

EXAMPLE 6

Triplex Stability in the Presence of Potassium

At 1 mM $MgCl_2$ and 0 mM KCl, ODNs containing several positively-charged internucleoside linkages were superior to their unmodified counterpart in triplex formation. The formation of triplex DNA in the presence of $K^+$, however, is crucial if these oligonucleotides are useful in inhibiting gene expression within a cell whether in culture or within an organism. Positively-charged ODNs P-1 and P-2 are compared to U-1 at 2 concentrations each of both $MgCl_2$ and KCl. The ODN concentration used was 200 nM. Oligonucleotide U-1 was examined using 1 mM and 10 mM $MgCl_2$, while oligonucleotides P-1 and P-2 were examined at the more stringent conditions of 0.1 $MgCl_2$ and 1 mM $MgCl_2$. A trace amount of shifted duplex was seen by gel shift assay with ODN U-1 at 10 mM $MgCl_2$, but not at 1 mM $MgCl_2$. In contrast, ODNs P-1 and P-2 formed triplex DNA at both 0.1 $MgCl_2$ and 1 mM $MgCl_2$. In both cases, there was only a slight increase in triplex at 1 mM $MgCl_2$ compared to 0.1 mM $MgCl_2$. The response of P-1 compared to P-2 with respect to $K^+$ inhibition was striking, especially at 1 mM $MgCl_2$. Triplex DNA formation seen with P-2 at 1 mM $MgCl_2$ and 100 mM KCl was approximately 80% of that seen without KCl. In contrast, triplex DNA formed with P-2 at 0.1 mM $MgCl_2$ and 100 mM KCl was reduced to less than 60% of that seen without KCl. This monovalent cation-inhibition of triplex formation is similar to that reported by other laboratories with unmodified ODNs (Milligan, et al., *Nucleic Acids Res.*, 21:327–333, 1993; Cheng, A. J., et al., *Nucleic Acids Res.*, 21:5630–5635, 1993; Olivas, et al., *Biochem.*, supra).

EXAMPLE 7

Triplex Formation in the Presence of Monovalent Cations

Triplex formation in the presence of LiCl, NaCl, and KCl was evaluated to determine whether the observed triplex inhibition was potassium-specific or resulted from increases in the ionic strength of the solution. ODN P-2 was studied at a concentration of 2 μM with a $Mg^{2+}$ concentration of 0.1 mM using 40 mM, 80 mM, and 120 mM concentrations of LiCl, NaCl, or KCl. Triplex formation was least affected by increasing concentrations of LiCl. NaCl caused an intermediate level of inhibition and KCl had the greatest effect on triplex formation. This pattern of monovalent cation inhibition was identical to that seen with unmodified ODNs suggesting a similar mode of association of the oligonucleotide to the duplex.

EXAMPLE 8

Triplex Formation Using Oligonucleotides With Extensive Cationic Phosphoramidate Modifications The effect of extensive ODN modification on triplex formation was examined with oligonucleotides containing 88% modified linkages or 100% cationic phosphoramidate modified linkages (P-3 and P-4, respectively). The ability of ODNs P-3 and P-4 to associate with Duplex I (SEQ ID NO:1) was compared to that of compounds U-1 and P-2. The assay was performed using 130 mM $K^+$ and 1 mM $Mg^{2+}$, concentrations that approximate physiologic salt concentrations. The ODN concentrations used were 20 nM, 200 nM, and 2 μM. Samples were processed with the various oligonucleotides at the various concentrations and a sample containing no oligonucleotide was used as a background control. Shading in the control lane, located in the region where the triplex band migrated, was subtracted from the triplex bands during data analysis. Triplex formation with U-1 was essentially undetectable under the concentrations tested. Both P-3 and P-4 showed a greater affinity and, therefore, improved stability, for Duplex I than did P-2. The disassociation constants for triplex formation were $8 \times 10^{-7}$ M for P-2, $1 \times 10^{-7}$ M for P-4, and $7 \times 10^{-8}$ M for P-3. The migration of the triplex formed with P-3 was slightly slower than that with P-2, a result of the increased cationic nature of P-3.

EXAMPLE 9

Triplex Formation Under Stringent Salt Conditions

The effect of increasing KCl concentrations on triplex formation was also assessed. Oligonucleotides P-2 and P-3 were incubated with Duplex I (SEQ ID NO:1) under increasing concentrations of KCl (0, 50, 100, 150, 200, and 250 mM). The concentration of $MgCl_2$ was held at 1 mM and the ODN concentration was 2 μM. Increasing concentrations of KCl gradually reduced the amount of triplex DNA observed for oligonucleotide P-2; however, significant triplex formation was observed at physiologic levels of potassium. The inhibitory effect of KCl appeared to plateau at 200 mM, as no further triplex inhibition was observed at 250 mM. Triplex formation with ODN P-3 was significantly less sensitive to $K^+$ concentration. In fact, at 250 mM KCl, almost 90% of Duplex I (SEQ ID NO:1) remained in the triplex form. Increasingly positively-charged internucleoside linkages from 11 of 16 (69%) in P-2 to 14 of 16 (88%) in P-3 is associated with a significant decrease in potassium-mediated inhibition of triplex formation.

EXAMPLE 10

Magnesium Requirements for Triplex Formation $Mg^{2+}$ is known to stabilize traditional triplex DNA. The effect of decreasing $Mg^{2+}$ and increasing $K^+$ on triplex formation was assessed using ODNs P-2 and P-3 by gel shift assay. In the absence of $K^+$, triplex formation with both P-2 and P-3 was essentially unaffected by $Mg^{2+}$ concentrations ranging from 0 to 1 mM. Triplex formation was greater than 80%, even in the absence of $Mg^{2+}$. Although increased, $Mg^{2+}$ concentration had no effect on the amount of triplex formed with P-3, in the absence of $K^+$ a small fraction of the triplex DNA changed to a more rapidly migrating form with increased $Mg^{2+}$. The appearance of this band with intermediate electrophoretic mobility suggests the possibility of different conformations of triplex DNA. In 130 mM KCl, triplex formation with ODN P-2 became sensitive to $Mg^{2+}$ concentration. There was a significant reduction in triplex DNA formed with oligonucleotide P-2 as $Mg^{2+}$ decreased from 1 mM to 0 mM. Triplex formation with P-3 remained essentially independent of $Mg^{2+}$ concentration in the presence of physiologic concentrations of KCl.

EXAMPLE 11

Oligonucleotide Specificity for Target DNA

Oligonucleotide P-4 was used to examine the specificity of the oligonucleotide for its target versus a random oligonucleotide such as Duplex II (SEQ ID NO:3). The nonspecific interaction of oligonucleotides U-1 and P-4 with the nontarget Duplex II (SEQ ID NO:3) in the presence of either 1 mM or 10 mM $MgCl_2$ and in the absence of KCl were assessed by gel shift analysis. Binding of U-1 to Duplex II (SEQ ID NO:3) was not detected and nonspecific interactions between P-4 and Duplex II (SEQ ID NO:3) were not detected at ODN concentrations of 20 nM to 200 nM of oligonucleotide. The complex formed at about equal levels at both 10 mM $Mg^{2+}$ and 1 mM $Mg^{2+}$, indicating a lack of $Mg^{2+}$ dependence in this range of ion concentration. To further investigate these nonspecific interactions under salt concentrations more closely resembling in vivo conditions, the experiment was repeated in 130 mM KCl. Under conditions approximating physiologic, oligonucleotide U-1 again showed no evidence of binding to Duplex II (SEQ ID NO:3) at either 1 mM or 10 mM $Mg^{2+}$. At an ODN concentration of 2 μM, the extent of nonspecific binding of P-4 to Duplex II (SEQ ID NO:3) was greatly attenuated by increasing the $K^+$ concentration of the triplex buffer. In both cases, the degree of nonspecific binding was too low for accurate quantitation. The decrease in nonspecific binding seen in 130 mM KCl was likely related to a general increase in ionic strength, however, it is also possible that there was a specific effect of $K^+$.

To continue the analysis of the specificity of cationic oligonucleotide binding, mismatches were positioned along the target to identify areas where matching was critical or alternatively, where mismatching would be targeted. The original target sequence was a DNA duplex (SEQ ID NO:4) and SEQ ID NO:20:

5' AGTTTTGTGTCCCCCTCTCAGGTGTCACAG 3'

3' TCAAAACACAGGGGGAGAGTCCACAGTGTC 5'

The triplex forming oligonucleotide was:

5' AAAATATAGGGGGAGAG 3' (SEQ ID NO:5)

Varying targets tested:

M1 (SEQ ID NO:6) and SEQ ID NO:21

5' AGTTTTGTGTCCgCCTCTCAGGTGTCACAG 3'

3' TCAAAACACAGGcGGAGAGTCCACAGTGTC 5'

M2 (SEQ ID NO:7) and SEQ ID NO:22

-continued

```
5'  AGTTTTGTGTCggCCTCTCAGGTGTCACAG  3'
3'  TCAAAACACAGccGGAGAGTCCACAGTGTC  5'

M3  (SEQ ID NO:8) and SEQ ID NO:23

5'  AGTTTTGTGTCgggCTCTCAGGTGTCACAG  3'
3'  TCAAAACACAGcccGAGAGTCCACAGTGTC  5'

M4  (SEQ ID NO:9) and SEQ ID NO:24

5'  AGTTTTGTGTCggggTCTCAGGTGTCACAG  3'
3'  TCAAAACACAGccccAGAGTCCACAGTGTC  5'

E1  (SEQ ID NO:10) and SEQ ID NO:25

5'  AGTTTgGTGTCCCCCTCTCAGGTGTCACAG  3'
3'  TCAAAcCACAGGGGGAGAGTCCACAGTGTC  5'

E2  (SEQ ID NO:11) and SEQ ID NO:26

5'  AGTTggGTGTCCCCCTCTCAGGTGTCACAG  3'
3'  TCAAccCACAGGGGGAGAGTCCACAGTGTC  5'

E3  (SEQ ID NO:12) and SEQ ID NO:27

5'  AGTgggGTGTCCCCCTCTCAGGTGTCACAG  3'
3'  TCAcccCACAGGGGGAGAGTCCACAGTGTC  5'

E4  (SEQ ID NQ:13) and SEQ ID NO:28

5'  AGggggGTGTCCCCCTCTCAGGTGTCACAG  3'
3'  TCccccCACAGGGGGAGAGTCCACAGTGTC  5'
```

The results of these triplex formations were assessed using gel shift assays. Target oligonucleotide was assayed in the presence of cationic Oligonucleotide with concentration changes between 2 nM and 20 μM. Radioactively endlabelled target duplex was used at a concentration of 0.2 nM. Oligonucleotides and duplex were incubated at 22° C. for 1 hour in 1 mM $MgCl_2$, 130 mM KCl, 100 mM Tris, pH 7.5 prior to analysis on a 15% polyacrylamide gel using TBM buffer (supra). Results indicated that the formation of triplex was less tolerant to alterations in the middle of the target region, although 13 consecutive nucleotide interactions (as will be understood by those of ordinary skill in the art of triplex formation, for example for the following nucleic acid base pair matches; an A or T is matched to an A, a G to a G, and a T to a C) only marginally reduced stability as compared to 17 consecutive nucleotide interactions.

When the M1 or E4 target sequences were tested in vivo using reporter plasmids (target inserted after the transcription start site but before the translational start), as described in Example 17, the Ml target site did not support triplex formation. Therefore, for a 17 mer and a single oligonucleotide (in contrast to a bipartite oligonucleotide), 10 consecutive triplex forming matches was insufficient to inhibit transcription. In an embodiment with a 17 mer oligonucleotide there are at least 10 consecutive matches. The E4 sequence was only marginally effective, indicating that full inhibition may require more than 13 consecutive matches in vivo. These results suggest that a reasonably high degree of specificity can be expected from the cationic triplex forming oligonucleotides. These experiments help to define the thermodynamic constraints of the oligonucleotide. For example, using a 10 mer, on skilled in the art can calculate the binding constant of the oligonucleotide to its target and know that new oligonucleotides for testing should have a greater binding constant.

EXAMPLE 12

Toxicity and Stability Testing of Oligonucleotide for Target Cell

As an example of a method to determine whether or not phosphoramidate-modified oligonucleotides are stable to target cells containing the target duplex DNA, Xenopus embryos were microinjected with varying concentrations of oligonucleotide. *Xenopus laevis* were purchased from Xenopus I (Ann Arbor, Mich.). Eggs were obtained from mature frogs fertilized in vitro and maintained in 0.1× MBSH (Colman, et al., (1984) In Hames, D. and Higgins, S. (ed.), *Transcription and translation—A Practical Approach*, IRL Press, Oxford, pp. 271–302). Oligonucleotides were introduced by microinjection into the cytoplasm of the embryos as described by Colman (supra). To study the degradation of the oligonucleotides, at various times following injection of labeled oligonucleotides (see Example 2), the injected embryos were frozen in dry ice and thawed in 200 μl chloroform and 400 μl 0.2% SDS, the phenol layer was extracted with water twice more. Aqueous fractions were pooled, extracted once with chloroform, and dried in a SpeedVac Concentrator. The residue was resuspended in water and the amount of radioactivity was determined by scintillation counter or analyzed by electrophoresis using a 20% polyacrylamide-7M urea gel which was subsequently exposed at −70° C. to Kodak X-OMAT AR file with an intensifying screen.

As an example of determining the cellular toxicity of the oligonucleotides, various concentrations of oligonucleotide were microinjected into matched cell samples. Defects in activation of gene expression, reflecting toxicity related to general inhibition of transcription, was assessed by looking at the activation of specific genes that were expressed at the 4000 cell stage including GS17 or EF-Iα gene expression. In addition, defects in gastrulation, neurulation, or other early developmental events serves as a sensitive measure of nonspecific toxicity; therefore, this model was useful to test toxicity for oligonucleotides in general. (See Vize, et al., *Methods in Cell Biol.*, 36:367–387, 1991). Embryos obtained as outlined in Weeks, et al. (1991, supra), have been injected with up to 10 ng of modified oligonucleotides as described herein without nonspecific toxic affects. Higher concentrations of oligonucleotide have also been tested, some without toxic effect. Further, experiments to determine the toxic dose of these modified oligonucleotides in vivo are under way. Uninjected and control injected (injection buffer alone) embryos are compared to oligonucleotides injected using groups of 50 embryos in experiments performed in triplicate. Defects are noted by comparison to *Xenopus laevis* normal tables (Nieuwkoop, et al. (1967), *Normal table of Xenopus laevis* (Daudin), North Holland Publishing Co., Amsterdam).

EXAMPLE 13

Effect of Oligonucleotides on Gene Expression

The most direct way of examining the effect of a TFO on gene expression is to measure RNA levels derived from the gene that is targeted. This measurement might be made by sampling tissue and extracting RNA followed by Northern blot analysis, RNase protection assays, or Reverse transcriptase PCR. All techniques are well known in the art and discussed in detail in *Molecular Cloning: A Laboratory Manual* (Sambrook, et al., 1989, Cold Spring Harbor Laboratory, Cold Spring, N.Y.).

Alternatively, levels of RNA can be examined by in situ analysis of tissues of interest. These techniques are also known in the art. A less direct, but often useful, way to look at transcription is to assay for the protein products of the gene. This would include Western analyses, polyacrylamide gel electrophoresis, and a variety of antibody based strategies including radioimmunoassays and enzyme linked immunoadsorbent assays. All well known in the art. Sensitive measures of protein levels both from extracted tissue (including blood) or immunohistochemistry are known in the art. The effectiveness of introducing triplex forming oligonucleotides into the bloodstream (as described for clinical trials on antisense oligonucleotides for AIDS therapy) or at the site of tumor growth can be assayed by regression of tumor size, or by sampling the tumor for decreases in growth rate, induced apoptotic events, or changes in myc RNA levels.

EXAMPLE 14

Using TFOs to Alter the Expression of the Myc Oncogene

One of the most common oncogenes expressed in transformed cells is the c-myc oncogene. In vitro inhibition of the c-myc oncogene has been reported (Kim, H-G and Miller, D. (1995), "Inhibition of In vitro transcription by a triplex forming oligonucleotide targeted to human c-myc P2 promoter," Biochemistry 34, 8165–8171). The oligonucleotides AGGGAGGGAGGTAAGAAAAAGGG (SEQ ID NO:15) and GGGAAAAAGAATGGAGGGAGGGA (SEQ ID NO:16) are prepared having 87% of the linkages substituted with N,N-diethyl-ethylenediamine as disclosed in Example 1. Triplex formation is demonstrated by electrophoretic mobility shift analysis of triplex formation and DNase I foot-printing as disclosed by Kim, et al. (supra). In vitro transcription alteration is performed using a HeLa nuclear extract in vitro transcription system (Promega) as disclosed by Kim, et al.

EXAMPLE 15

Deliverable Concentrations of Oligonucleotides are Sufficient to Promote Triplex Formation Our results indicated that little non-specific toxicity was seen when 10 ng of oligonucleotide was injected into embryos. Assuming an even distribution inside the cells, this corresponds to a concentration of 2 $\mu$M oligonucleotide. Can triplex form when the concentration of oligonucleotide is 2 $\mu$M or less and how fast will it form? 2 fmol of duplex was added to a 2 $\mu$M solution of oligonucleotide in 130 mM KCl and 1 mM MgCl$_2$, 150 mM Tris (pH 7.5), with 1 $\mu$g of competitor nucleic acid at 22° C. The mix was sampled at 4 minute intervals between 0 min and 68 min by taking an aliquot of the mix and directly loading it onto a 15% polyacrylamide gel in TBM buffer already conducting a current of 40 mAmp. This allows an instant separation of the cationic oligonucleotide from the more anionic duplex and triplex. The extent of triplex formation was determined by the direct quantitation of the duplex to triplex ratio using a Packard Instant imager at the end of the assay. In less than 2 min more than 50% of the duplex was converted to triplex. Results are provided in FIG. 2.

Thus, at concentrations of oligonucleotide estimated to be analogous to what is routinely injected into embryos, triplex formation was very rapid. The rapid formation was needed to compete with other cellular components competing for the same binding site.

EXAMPLE 16

Cationic Phosphoramidate Oligonucleotides can Specifically Compete with Cellular Transcription Factors Changes in electrophoretic mobility during gel electrophoresis can be used to demonstrate either protein interaction with duplex DNA or oligonucleotide mediated triplex formation. In a binding competition, the unique mobility of duplex DNA alone, oligonucleotide mediated triplex or a protein:DNA complex allowed each to be identified. When the duplex DNA containing the recognition site for OZ-protein binding (SEQ ID NO:1) is labeled with 32P, quantitation of each band on the gel allowed comparison of the level of each complex. Duplex DNA was present at 1 ng and was mixed with a cellular extract (2 $\mu$g/$\mu$l, from stage VI *Xenopus oocytes*) containing sufficient OZ protein to shift the mobility of half of the duplex. Addition of sequence specific oligo (SEQ ID NO:2) between 20 nM and 20 $\mu$M lead to a triplex forming oligonucleotide concentration dependent loss of the OZ protein/DNA interaction, while non-specific cationic oligonucleotide (ERV sequence) at 20 $\mu$M did not.

EXAMPLE 17

In vivo Expression of an SV40/CAT Plasmid is Inhibited when a Triplex Forming Target and Cationic Oligonucleotide are Present The efficacy of triplex formation by cationic oligonucleotides was assayed by studying the ability of modified oligonucleotides to block transcription of a reporter plasmid in Xenopus oocytes. Two reporter plasmids were used that contained the SV40 early promoter controlling the synthesis of chloramphenicol acetyl transferase (CAT). One was the Promega pCAT (Madison, Wis.) control vector (includes the SV40 promoter and enhancer) and a derivative of pCAT control with the GS-17 triplex target (SEQ ID NO:1) 30 base pairs after the transcriptional start site (at a unique StuI restriction site), but before the AUG that signals the start of translation. pSV-β-galactosidase was coinjected with the CAT-containing plasmids to provide an independent indication of transcriptional activity. CAT assays were carried out as recommended by the manufacturer (Promega, supra).

Figure 4:
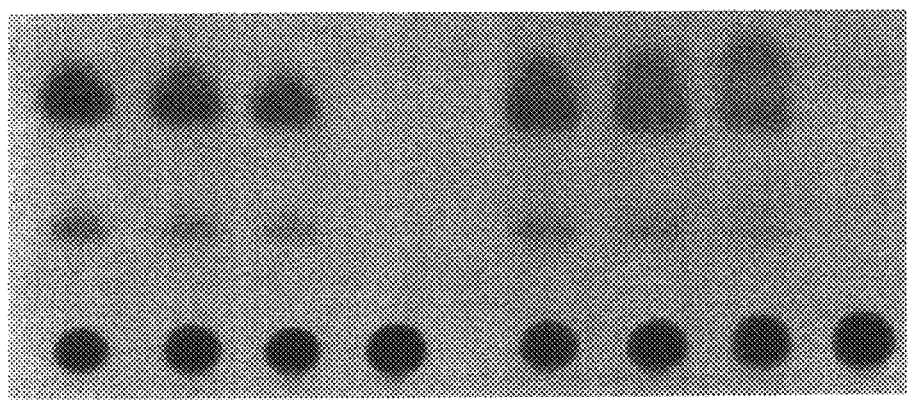
FIG. 4 illustrates the results of a Northern blot demonstrating that triplex formation inhibits CAT transcription in oocyte nuclei.

Results (see FIG. 4) indicated that in vivo expression of an SV40/CAT plasmid was inhibited when a triplex forming target and cationic oligo were present. *Xenopus oocytes* were injected with 3.2 fmol of the pCAT-control vector with or without 0.89 pmol of cationic triple target oligo (SEQ ID NO:2). Plasmid and vector were preincubated for 1 hr prior to injection. All samples were coinjected with 3.2 fmol of pSV-β-galactosidase and β-galactosidase measured and compared to the pCAT-control vector alone. Results indicated a reduction in CAT transcription of 20–50 fold in the presence of the triplex forming oligonucleotide. In similar studies, little or no affect was observed in duplicate experiments using unmodified oligonucleotide.

Sequential addition of oligonucleotide and target can make a difference. In these experiments, a 300 fold molar excess of oligonucleotide was used. When the oligonucleotide was injected into the nucleus and 30 min later reporter plasmid was injected, the specific modified oligonucleotide reduced CAT activity to between one-half to one-third of control values. When the plasmid was injected first, the oligonucleotide did not inhibit CAT activity in this assay.

These assays suggest that once plasmid DNA has been assembled into chromatin, triplex formation may be compromised. However, if the oligonucleotide is present when chromatin is assembling, the oligonucleotide can inhibit transcription even when the molar ratio of histone to oligonucleotide is very similar.

That oligonucleotide can inhibit transcription when chromatin is assembling was determined using the oligonucleotides of this invention targeted to endogenous enhancer regions in Xenopus embryos. In these trials, 25 ng of oligonucleotide were injected per embryo. The triplex target was the endogenous GS17 enhancer (SEQ ID NO:1, designated OZ in FIG. 1B) or an endogenous region adjacent to it (SEQ ID NO:3, designated ERV I (SEQ ID NO:3). TFOs used were either SEQ ID NO:2 (provided in the 5' to 3' orientation) in FIG. 1B (OZ oligos) or for ERV, a 17 mer with the sequence GGAATAAAGGGGAGGGG (SEQ ID NO:17) was used (in the 3'-5' orientation). The oligonucleotides with this sequence were prepared using either N,N-diethyl ethylenediamine modified linkages or N-dimethylaminopropyl modified linkages with all linkages modified. The activation of the GS17 gene in embryos injected with 25 ng of cationic oligonucleotide was assayed 12 hours after fertilization. Four different fully modified cationic oligonucleotides were used; two different internucleoside linkage modifications to two different targets. A control CON-DEED (5'AGGAGGAGGAGATGAGGAGGG 3', SEQ ID NO: 14) was also used. This oligonucleotide is a fully modified 21 mer of unrelated but mixed purine sequence. The result of positively modified oligonucleotides, either N,N-diethyl ethylenediamine modified linkages or N-dimethylaminopropyl modified linkages indicated that a greater than 50% reduction in transcriptional activation of the GS17 gene was achieved. Slightly less, but an easily measurable effect was seen when the ERV sequence was targeted for triplex formation. We note that initial attempts to inhibit GS17 gene expression using neutral oligonucleotide modifications (methoxyethylphosphoramidate linkages) were not successful. Identically treated siblings of those used for RNA isolation developed into swimming tadpoles with no apparent deformities indicating that the oligonucleotide tested was nonspecifically nontoxic.

EXAMPLE 18

Duplex Studies

The sequences of the oligonucleotides used in these studies are found in FIG. 1B. To form duplex DNA, 1 nmol of target oligonucleotides was mixed with 1 nmol of each modified oligonucleotide to be tested. Three different conditions were tested, 150 nM NaCl/10 mM NaPO4, 10% formamide or 500 mM urea. The reactions comprising the different solutions, duplex DNA and target were heated to 85° C. for 5 minutes and cooled slowly to room temperature. Absorbance of the oligonucleotide solutions were measured every 0.5° C. from 15° C. to 75° C. at 260 nM using a Gilford Model Response II thermal spectrophotometer. Melting temperature was obtained from the maximum value of the first derivative plots of absorbance vs. temperature.

Duplexes formed with an unmodified complementary strand of the oligonucleotides listed in FIG. 1 have the following thermal denaturation profiles in 150 nM NaCl/10 mM NaPO4, 10% formamide or 500 mM urea.

TABLE I

| | Melting Temperature (Tm) in ° C. | | |
|---|---|---|---|
| Oligo | 150 nM NaCl | 10% formamide | 500 nM urea |
| U-1 | 52 | 29 | 31 |
| N-1 | 40.5 | 22.5 | 24 |
| N-2 | 42 | 24 | 29 |
| P-1 | 49.5 | 44 | 48.5 |

In 150 mM NaCl, unmodified oligonucleotides and cationic oligonucleotides both had Tm's of about 50° C., however, as salt concentration was lowered to 0 mM NaCl, unmodified oligonucleotides exhibited a decreasing Tm while the oligonucleotides of this invention with 100% modified internucleoside linkages were unaffected. Thus, the formation of duplex using oligonucleotides with the internucleoside linkages of this invention formed duplexes with target nucleic acid independent of salt concentration.

EXAMPLE 19

Cationic Oligonucleotides as Antisense Agents and Targets for Nuclease Activity The oligonucleotides of this invention can act as mediators for mRNA degradation. Although a variety of maternally inherited mRNAs have been depleted using antisense oligonucleotides, currently available modifications have been unable to diminish mRNAs transcribed in the embryo.

We targeted the GS-17 transcript using a 17 mer with cationic modifications according to this invention (in one example, N,N-diethyl ethylenediamine modified linkages using the SEQ ID NO:1 oligo). In the experiment, the cationic modifications were positioned at the 5' and the 3' ends of the oligo with an area of 6 consecutive phosphodiester bonds positioned between the cationic modifications to support the activity of RNase H. In these experiments, fertilized Xenopus eggs were injected with N,N-diethyl ethylenediamine-modfied oligo complementary to the translational start site of the GS17 mRNA (16 ng, 8 ng, 4 ng, or 2 ng of oligo injected). The level of GS17 mRNA was an analyzed 12 hours after injection by isolation as described in Weeks et al. (1991, supra), followed by Northern blot analysis. EF1-α (GenBank Accession No. M25504) was used as a non-related control transcript. Results indicated a dramatic difference between the level of GS17 mRNA in control injected and oligonucleotide injected embryos and the degradation was dose dependent on the amount of oligonucleotide present.

It will be appreciated that certain variations to this invention may suggest themselves to those skilled in the art. The foregoing detailed description is to be clearly understood as given by way of illustration, the spirit and scope of this invention being limited solely by the appended claims.

What is claimed is:

1. A triplex-forming oligonucleotide comprising about 30% to about 100% cationic alkylpolyamine internucleoside linkages.

2. The oligonucleotide of claim 1, wherein the oligonucleotide comprises ethylenediamine-class phosphoramidate internucleoside linkages.

3. The oligonucleotide of claim 1, wherein the oligonucleotide comprises dimethylamino propylamine linkages or diethylethylenediamine linkages.

4. The oligonucleotide of claim 2 wherein the triplex forming oligonucleotide is also a duplex forming oligonucleotide.

5. The oligonucleotide of claim 4 wherein the duplex forming oligonucleotide comprises ethylenediamine-class linkages and mixed chirality dimethylamino propylamine linkages and not N,N,N'-trimethylethylenediamine or 4-(2-aminoethyl)morpholine linkages.

6. The oligonucleotide of claim 4 wherein the oligonucleotide has N-ethylethylenediamine phosphoramidate internucleoside linkages or N, N-diethylethylenediamine phosphoramidate internucleoside linkages.

7. The oligonucleotide of claim 1 wherein the oligonucleotide is at least 12 nucleotides in length.

8. The oligonucleotide of claim 1 further comprising at least one other modified internucleoside linkage.

9. The oligonucleotide of claim 7 wherein the oligonucleotide has at least one ethylenediamine phosphoramidate internucleoside linkage.

10. The oligonucleotide of claim 7 wherein the oligonucleotide has at least one diethylethylenediamine phosphoramidate internucleoside linkage.

11. An oligonucleotide comprising at least about 30% cationic phosphoramidate internucleoside linkages and at least about 4 bases with RNase H sensitive internucleoside linkages positioned between the cationic phosphoramidate internucleoside linkages.

12. The oligonucleotide of claim 11 wherein the oligonucleotide includes at least about 6 bases with RNase H sensitive internucleoside linkages positioned between the cationic phosphoramidate internucleoside linkages.

13. The oligonucleotide of claim 11 wherein there are at least about 4 bases with cationic phosphoramidate internucleoside linkages positioned at a 5' end of the oligonucleotide and at least about 4 bases with cationic phosphoramidate internucleoside linkages positioned at a 3' end of the oligonucleotide.

14. A method for cleaving an RNA molecule comprising the steps of: contacting an RNA molecule in a cell with an oligonucleotide comprising at least about 30% cationic phosphoramidate internucleoside linkages and at least about 4 bases with RNase H sensitive internucleoside linkages positioned between the cationic phosphoramidate internucleoside linkages.

15. A method for binding an oligonucleotide to a nucleic acid polymer comprising the steps of:

preparing a triplex-forming oligonucleotide comprising about 30% to about 100% cationic alkylpolyamine internucleoside linkages; and contacting the oligonucleotide with the nucleic acid polymer.

16. The method of claim 15 wherein the nucleic acid polymer is RNA or DNA.

17. The method of claim 15 wherein the nucleic acid polymer is double stranded or single stranded.

18. The method of claim 15 further comprising the step of denaturing the nucleic acid polymer.

19. The method of claim 18 wherein the denaturing step comprises exposing the nucleic acid polymer to heat, a denaturing concentration of salt, or a chaotropic agent.

20. The method of claim 15 wherein the nucleic acid is DNA and the contacting step forms a triplex.

21. The method of claim 15 wherein the nucleic acid is RNA and the contacting step forms a duplex.

22. The method of claim 15 wherein the method further comprises introducing the oligonucleotide into a cell.

23. A method for limiting transcription from a gene comprising the steps of:

preparing a triplex-forming oligonucleotide comprising about 30% to about 100% cationic alkylpolyamine internucleoside linkages and capable of specifically hybridizing to at least a portion of a gene; and contacting the oligonucleotide with double stranded DNA comprising the gene, wherein the oligonucleotide binds to at least a portion of the gene to reduce the level of RNA production from the gene.

24. The method of claim 23 wherein the oligonucleotide binds to a region of the gene selected from the group of an open reading frame, a promoter or an enhancer.

25. The method of claim 23, wherein the oligonucleotide comprises ethylenediamine-class phosphoramidate internucleoside linkages.

26. The method of claim 25, wherein the oligonucleotide comprises dimethylamino propylamine linkages or diethylethylenediamine linkages.

27. The method of claim 25 wherein the method further comprises introducing the oligonucleotide into a cell.

28. The method of claim 27 wherein the introducing step comprises a method selected from the group of microinjection and lipid-mediated introduction.

29. A triplex-forming oligonucleotide comprising a tag and about 30% to about 100% cationic alkylpolyamine internucleoside linkages.

30. The oligonucleotide of claim 29 wherein the tag is selected from the group of enzymatic tags, radiolabeled tags and fluorescent tags.

31. A method for limiting transcription from a gene comprising the steps of:

preparing an oligonucleotide comprising at least one cationic alkylpolyamine internucleoside linkage and capable of specifically hybridizing to at least a portion of a gene; and contacting the oligonucleotide with double stranded DNA comprising the gene, wherein the oligonucleotide binds to at least a portion of the gene to reduce the level of RNA production from the gene.

* * * * *